(12) United States Patent
Lowe et al.

(10) Patent No.: US 9,101,503 B2
(45) Date of Patent: Aug. 11, 2015

(54) APPARATUS HAVING VARIABLE STRUT LENGTH AND METHODS OF USE

(75) Inventors: David Lowe, Redwood City, CA (US); Craig Bonsignore, Pleasanton, CA (US); David W. Snow, San Carlos, CA (US); Timothy Robinson, Sandown, NH (US); Joshua P. Wiesman, Wayland, MA (US); Dawn Henderson, Santa Clara, CA (US); Nathan Maier, Haward, CA (US)

(73) Assignee: J.W. MEDICAL SYSTEMS LTD., Weihai Shandong (CN)

( * ) Notice: Subject to any disclaimer, the term of this patent is extended or adjusted under 35 U.S.C. 154(b) by 686 days.

(21) Appl. No.: 12/043,513

(22) Filed: Mar. 6, 2008

(65) Prior Publication Data
US 2009/0228088 A1  Sep. 10, 2009

(51) Int. Cl.
*A61F 2/06* (2013.01)
*A61F 2/915* (2013.01)
*A61F 2/91* (2013.01)
(Continued)

(52) U.S. Cl.
CPC . *A61F 2/915* (2013.01); *A61F 2/91* (2013.01); *A61F 2/966* (2013.01); *A61F 2/89* (2013.01); *A61F 2002/9155* (2013.01); *A61F 2002/91508* (2013.01); *A61F 2002/91533* (2013.01);
(Continued)

(58) Field of Classification Search
CPC . A61F 2/91; A61F 2/915; A61F 2002/91508; A61F 2002/91533; A61F 2002/91541; A61F 2002/9155; A61F 2002/91558
USPC ................................................ 623/1.15–1.22
See application file for complete search history.

(56) References Cited

U.S. PATENT DOCUMENTS

| 4,069,825 A | 1/1978 | Akiyama |
| 4,468,224 A | 8/1984 | Enzmann et al. |

(Continued)

FOREIGN PATENT DOCUMENTS

| CN | 1856280 A | 11/2006 |
| DE | 1 953 1659 | 3/1997 |

(Continued)

OTHER PUBLICATIONS

International Search Report and Written Opinion of PCT Application No. PCT/US2009/034889, dated Apr. 22, 2009, 13 pages total.

(Continued)

*Primary Examiner* — Jonathan W Miles
*Assistant Examiner* — Todd J Scherbel
(74) *Attorney, Agent, or Firm* — Kilpatrick Townsend & Stockton LLP

(57) ABSTRACT

A tubular prosthesis has a plurality of tubular rings that are radially expandable from a contracted configuration to an expanded configuration. Each ring comprises a plurality of axially oriented struts that are interconnected so as to form a circumferential series of at least one high peak and at least one low peak. The high and low peaks have apices that are oriented in the same axial direction. The apices of the high and low peaks are also oriented in the same direction and the apices of the high peaks are axially offset from the apices of the low peaks. A bridge member couples a pair of adjacent tubular rings together. The bridge member has a first end connected to a first low peak in a first tubular ring and a second end connected to either a high or low peak in an adjacent tubular ring.

64 Claims, 14 Drawing Sheets

(51) Int. Cl.
*A61F 2/966* (2013.01)
*A61F 2/89* (2013.01)

(52) U.S. Cl.
CPC .................. A61F2002/91541 (2013.01); A61F 2002/91558 (2013.01)

(56) References Cited

U.S. PATENT DOCUMENTS

| | | |
|---|---|---|
| 4,512,338 A | 4/1985 | Balko et al. |
| 4,564,014 A | 1/1986 | Fogarty et al. |
| 4,580,568 A | 4/1986 | Gianturco |
| 4,681,110 A | 7/1987 | Wiktor |
| 4,690,684 A | 9/1987 | McGreevy et al. |
| 4,733,665 A | 3/1988 | Palmaz |
| 4,739,762 A | 4/1988 | Palmaz |
| 4,748,982 A | 6/1988 | Horzewski et al. |
| 4,762,129 A | 8/1988 | Bonzel |
| 4,770,176 A | 9/1988 | McGreevy et al. |
| 4,775,337 A | 10/1988 | Van Wagener et al. |
| 4,776,337 A | 10/1988 | Palmaz |
| 4,886,062 A | 12/1989 | Wiktor |
| 4,891,225 A | 1/1990 | Langer et al. |
| 4,950,227 A | 8/1990 | Savin et al. |
| 4,988,356 A | 1/1991 | Crittenden et al. |
| 4,994,066 A | 2/1991 | Voss |
| 4,994,069 A | 2/1991 | Ritchart et al. |
| 4,994,298 A | 2/1991 | Yasuda |
| 5,013,318 A | 5/1991 | Spranza, III |
| 5,035,706 A | 7/1991 | Giantureo et al. |
| 5,040,548 A | 8/1991 | Yock |
| 5,061,273 A | 10/1991 | Yock |
| 5,064,435 A | 11/1991 | Porter |
| 5,092,877 A | 3/1992 | Pinchuk |
| 5,102,417 A | 4/1992 | Palmaz |
| 5,104,404 A | 4/1992 | Wolff |
| 5,122,154 A | 6/1992 | Rhodes |
| 5,135,535 A | 8/1992 | Kramer |
| 5,158,548 A | 10/1992 | Lau et al. |
| 5,192,297 A | 3/1993 | Hull |
| 5,195,984 A | 3/1993 | Schatz |
| 5,201,757 A | 4/1993 | Heyn et al. |
| 5,217,495 A | 6/1993 | Kaplan et al. |
| 5,219,355 A | 6/1993 | Parodi et al. |
| 5,226,913 A | 7/1993 | Pinchuk |
| 5,246,421 A | 9/1993 | Saab |
| 5,261,887 A | 11/1993 | Walker |
| 5,273,536 A | 12/1993 | Savas |
| 5,282,823 A | 2/1994 | Schwartz et al. |
| 5,282,824 A | 2/1994 | Gianturco |
| 5,300,085 A | 4/1994 | Yock |
| 5,312,415 A | 5/1994 | Palermo |
| 5,328,469 A | 7/1994 | Coletti |
| 5,334,187 A | 8/1994 | Fischell et al. |
| 5,391,172 A | 2/1995 | Williams et al. |
| 5,421,955 A | 6/1995 | Lau et al. |
| 5,443,498 A * | 8/1995 | Fontaine ..................... 623/1.17 |
| 5,445,646 A | 8/1995 | Euteneuer et al. |
| 5,456,713 A | 10/1995 | Chuter |
| 5,458,615 A | 10/1995 | Klemm et al. |
| 5,470,315 A | 11/1995 | Adams |
| 5,478,349 A | 12/1995 | Nicholas |
| 5,484,444 A | 1/1996 | Braunschweiler et al. |
| 5,490,837 A | 2/1996 | Blaeser et al. |
| 5,496,346 A | 3/1996 | Horzewski et al. |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,522,882 A | 6/1996 | Gaterud et al. |
| 5,527,354 A | 6/1996 | Fontaine et al. |
| 5,531,735 A | 7/1996 | Thompson |
| 5,533,968 A | 7/1996 | Muni et al. |
| 5,534,007 A | 7/1996 | St. Germain et al. |
| 5,545,209 A | 8/1996 | Roberts et al. |
| 5,549,551 A | 8/1996 | Peacock, III et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,571,086 A | 11/1996 | Kaplan et al. |
| 5,591,195 A | 1/1997 | Taheri et al. |
| 5,593,412 A | 1/1997 | Martinez et al. |
| 5,607,444 A | 3/1997 | Lam |
| 5,607,463 A | 3/1997 | Schwartz et al. |
| 5,628,755 A | 5/1997 | Heller et al. |
| 5,628,775 A | 5/1997 | Jackson et al. |
| 5,634,928 A | 6/1997 | Fischell et al. |
| 5,639,274 A | 6/1997 | Fischell et al. |
| 5,662,675 A | 9/1997 | Polanskyj Stockert et al. |
| 5,662,703 A | 9/1997 | Yurek et al. |
| 5,670,161 A | 9/1997 | Healy et al. |
| 5,676,654 A | 10/1997 | Ellis et al. |
| 5,683,451 A | 11/1997 | Lenker et al. |
| 5,690,644 A | 11/1997 | Yurek et al. |
| 5,693,085 A | 12/1997 | Buirge et al. |
| 5,697,948 A | 12/1997 | Marin et al. |
| 5,697,971 A | 12/1997 | Fischell et al. |
| 5,702,418 A | 12/1997 | Ravenscroft |
| 5,702,419 A | 12/1997 | Berry et al. |
| 5,709,701 A | 1/1998 | Parodi |
| 5,716,393 A | 2/1998 | Lindenberg et al. |
| 5,722,669 A | 3/1998 | Shimizu et al. |
| 5,723,003 A | 3/1998 | Winston et al. |
| 5,735,869 A | 4/1998 | Fernandez-Aceytuno |
| 5,741,323 A | 4/1998 | Pathak et al. |
| 5,749,848 A | 5/1998 | Jang et al. |
| 5,749,890 A | 5/1998 | Shaknovich |
| 5,749,921 A | 5/1998 | Lenker et al. |
| 5,755,697 A | 5/1998 | Jones et al. |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,792,144 A | 8/1998 | Fischell et al. |
| 5,797,951 A | 8/1998 | Mueller et al. |
| 5,800,519 A | 9/1998 | Sandock |
| 5,807,398 A | 9/1998 | Shaknovich |
| 5,824,040 A | 10/1998 | Cox et al. |
| 5,824,041 A | 10/1998 | Lenker et al. |
| 5,833,694 A | 11/1998 | Poncet |
| 5,836,964 A | 11/1998 | Richter et al. |
| 5,843,090 A | 12/1998 | Schuetz |
| 5,843,092 A | 12/1998 | Heller et al. |
| 5,855,563 A | 1/1999 | Kaplan et al. |
| 5,858,556 A | 1/1999 | Eckert et al. |
| 5,870,381 A | 2/1999 | Kawasaki et al. |
| 5,879,370 A | 3/1999 | Fischell et al. |
| 5,891,190 A | 4/1999 | Boneau |
| 5,895,398 A | 4/1999 | Wensel et al. |
| 5,899,935 A | 5/1999 | Ding |
| 5,902,332 A | 5/1999 | Schatz |
| 5,919,175 A | 7/1999 | Sirhan |
| 5,921,971 A | 7/1999 | Agro et al. |
| 5,922,020 A | 7/1999 | Klein et al. |
| 5,941,869 A | 8/1999 | Patterson et al. |
| 5,951,585 A | 9/1999 | Cathcart et al. |
| 5,961,536 A | 10/1999 | Mickley et al. |
| 5,965,879 A | 10/1999 | Leviton |
| 5,968,069 A | 10/1999 | Dusbabek et al. |
| 5,972,027 A | 10/1999 | Johnson |
| 5,976,107 A | 11/1999 | Mertens et al. |
| 5,976,155 A | 11/1999 | Foreman et al. |
| 5,980,484 A | 11/1999 | Ressemann et al. |
| 5,980,486 A | 11/1999 | Enger |
| 5,980,514 A | 11/1999 | Kupiecki et al. |
| 5,980,552 A | 11/1999 | Pinchasik et al. |
| 5,984,957 A | 11/1999 | Laptewicz, Jr. et al. |
| 5,989,280 A | 11/1999 | Euteneuer et al. |
| 5,993,484 A | 11/1999 | Shmulewitz |
| 5,997,563 A | 12/1999 | Kretzers et al. |

(56) References Cited

U.S. PATENT DOCUMENTS

| | | |
|---|---|---|
| 6,004,328 A | 12/1999 | Solar |
| 6,007,517 A | 12/1999 | Anderson |
| 6,010,530 A | 1/2000 | Goicoechea |
| 6,022,359 A | 2/2000 | Frantzen |
| 6,022,374 A | 2/2000 | Imran |
| 6,027,519 A | 2/2000 | Stanford |
| 6,033,434 A | 3/2000 | Borghi |
| 6,036,725 A | 3/2000 | Avellanet |
| 6,039,721 A | 3/2000 | Johnson et al. |
| 6,042,589 A | 3/2000 | Marianne |
| 6,050,999 A | 4/2000 | Paraschac et al. |
| 6,056,722 A | 5/2000 | Jayaraman |
| 6,063,111 A | 5/2000 | Hieshima et al. |
| 6,066,155 A | 5/2000 | Amann et al. |
| 6,068,655 A | 5/2000 | Seguin et al. |
| 6,070,589 A | 6/2000 | Keith et al. |
| 6,090,063 A | 7/2000 | Makower et al. |
| 6,090,136 A | 7/2000 | McDonald et al. |
| 6,102,942 A | 8/2000 | Ahari |
| 6,106,530 A | 8/2000 | Harada |
| RE36,857 E | 9/2000 | Euteneuer et al. |
| 6,120,477 A | 9/2000 | Campbell et al. |
| 6,120,522 A | 9/2000 | Vrba et al. |
| 6,123,712 A | 9/2000 | Di Caprio et al. |
| 6,123,723 A | 9/2000 | Konya et al. |
| 6,126,685 A | 10/2000 | Lenker et al. |
| 6,129,756 A | 10/2000 | Kugler |
| 6,132,460 A | 10/2000 | Thompson |
| 6,139,572 A | 10/2000 | Campbell et al. |
| 6,143,016 A | 11/2000 | Bleam et al. |
| 6,165,167 A | 12/2000 | Delaloye |
| 6,165,210 A | 12/2000 | Lau et al. |
| 6,171,334 B1 | 1/2001 | Cox |
| 6,179,878 B1 | 1/2001 | Duerig |
| 6,183,509 B1 | 2/2001 | Dibie |
| 6,187,034 B1 | 2/2001 | Frantzen |
| 6,190,402 B1 | 2/2001 | Horton et al. |
| 6,196,995 B1 | 3/2001 | Fagan |
| 6,200,337 B1 | 3/2001 | Moriuchi et al. |
| 6,217,585 B1 | 4/2001 | Houser et al. |
| 6,238,991 B1 | 5/2001 | Suzuki |
| 6,241,691 B1 | 6/2001 | Ferrera et al. |
| 6,241,758 B1 | 6/2001 | Cox |
| 6,248,122 B1 | 6/2001 | Klumb et al. |
| 6,251,132 B1 | 6/2001 | Ravenscroft et al. |
| 6,251,134 B1 | 6/2001 | Alt et al. |
| 6,254,612 B1 | 7/2001 | Hieshima |
| 6,254,628 B1 | 7/2001 | Wallace et al. |
| 6,258,117 B1 | 7/2001 | Camrud et al. |
| 6,264,688 B1 | 7/2001 | Herklotz et al. |
| 6,267,783 B1 | 7/2001 | Letendre et al. |
| 6,270,524 B1 | 8/2001 | Kim |
| 6,273,895 B1 | 8/2001 | Pinchuk et al. |
| 6,273,911 B1 | 8/2001 | Cox et al. |
| 6,273,913 B1 | 8/2001 | Wright et al. |
| 6,287,291 B1 | 9/2001 | Bigus et al. |
| 6,312,458 B1 | 11/2001 | Golds |
| 6,315,794 B1 | 11/2001 | Richter |
| 6,319,277 B1 | 11/2001 | Rudnick et al. |
| 6,322,586 B1 | 11/2001 | Monroe et al. |
| 6,325,823 B1 | 12/2001 | Horzewski et al. |
| 6,334,871 B1 | 1/2002 | Dor et al. |
| 6,340,366 B2 | 1/2002 | Wijay |
| 6,344,272 B1 | 2/2002 | Oldenburg et al. |
| 6,348,065 B1 | 2/2002 | Brown et al. |
| 6,350,252 B2 | 2/2002 | Ray et al. |
| 6,350,277 B1 | 2/2002 | Kocur |
| 6,357,104 B1 | 3/2002 | Myers |
| 6,361,558 B1 | 3/2002 | Hieshima et al. |
| 6,375,676 B1 | 4/2002 | Cox |
| 6,379,365 B1 | 4/2002 | Diaz |
| 6,383,171 B1 | 5/2002 | Gifford et al. |
| 6,394,995 B1 | 5/2002 | Solar et al. |
| 6,409,753 B1 | 6/2002 | Brown et al. |
| 6,415,696 B1 | 7/2002 | Erickson et al. |
| 6,416,543 B1 | 7/2002 | Hilaire et al. |
| 6,419,693 B1 | 7/2002 | Fariabi |
| 6,425,898 B1 | 7/2002 | Wilson et al. |
| 6,428,811 B1 | 8/2002 | West et al. |
| 6,451,025 B1 | 9/2002 | Jervis |
| 6,451,050 B1 | 9/2002 | Rudakov et al. |
| 6,464,720 B2 | 10/2002 | Boatman et al. |
| 6,468,298 B1 | 10/2002 | Pelton |
| 6,468,299 B2 | 10/2002 | Stack et al. |
| 6,485,510 B1 | 11/2002 | Camrud et al. |
| 6,488,694 B1 | 12/2002 | Lau et al. |
| 6,488,702 B1 | 12/2002 | Besselink |
| 6,511,468 B1 | 1/2003 | Cragg et al. |
| 6,520,986 B2 | 2/2003 | Martin et al. |
| 6,520,987 B1 | 2/2003 | Plante |
| 6,527,789 B1 | 3/2003 | Lau et al. |
| 6,527,799 B2 | 3/2003 | Shanley |
| 6,530,944 B2 | 3/2003 | West et al. |
| 6,540,777 B2 | 4/2003 | Stenzel |
| 6,551,350 B1 | 4/2003 | Thornton et al. |
| 6,555,157 B1 | 4/2003 | Hossainy |
| 6,558,415 B2 * | 5/2003 | Thompson .................... 623/1.16 |
| 6,562,067 B2 | 5/2003 | Mathis |
| 6,565,599 B1 * | 5/2003 | Hong et al. ................... 623/1.15 |
| 6,569,180 B1 | 5/2003 | Sirhan et al. |
| 6,575,993 B1 | 6/2003 | Yock |
| 6,579,305 B1 | 6/2003 | Lashinski |
| 6,579,309 B1 | 6/2003 | Loos et al. |
| 6,582,394 B1 | 6/2003 | Reiss et al. |
| 6,582,460 B1 | 6/2003 | Cryer |
| 6,585,756 B1 | 7/2003 | Strecker |
| 6,589,273 B1 | 7/2003 | McDermott |
| 6,592,549 B2 | 7/2003 | Gerdts et al. |
| 6,599,296 B1 | 7/2003 | Gillick et al. |
| 6,599,314 B2 | 7/2003 | Mathis |
| 6,602,226 B1 | 8/2003 | Smith et al. |
| 6,602,282 B1 | 8/2003 | Yan |
| 6,605,062 B1 | 8/2003 | Hurley et al. |
| 6,605,109 B2 | 8/2003 | Fiedler |
| 6,607,553 B1 | 8/2003 | Healy et al. |
| 6,613,074 B1 | 9/2003 | Mitelberg et al. |
| 6,629,992 B2 | 10/2003 | Bigus et al. |
| 6,645,517 B2 | 11/2003 | West |
| 6,645,547 B1 | 11/2003 | Shekalim et al. |
| 6,656,212 B2 | 12/2003 | Ravenscroft et al. |
| 6,660,031 B2 | 12/2003 | Tran et al. |
| 6,660,381 B2 | 12/2003 | Halas et al. |
| 6,663,660 B2 | 12/2003 | Dusbabek et al. |
| 6,666,883 B1 | 12/2003 | Seguin et al. |
| 6,676,693 B1 | 1/2004 | Belding et al. |
| 6,676,695 B2 | 1/2004 | Solem |
| 6,679,909 B2 | 1/2004 | McIntosh et al. |
| 6,685,730 B2 | 2/2004 | West et al. |
| 6,692,465 B2 | 2/2004 | Kramer |
| 6,699,280 B2 | 3/2004 | Camrud et al. |
| 6,699,281 B2 | 3/2004 | Vallana et al. |
| 6,699,724 B1 | 3/2004 | West et al. |
| 6,702,843 B1 | 3/2004 | Brown |
| 6,709,379 B1 | 3/2004 | Brandau et al. |
| 6,709,440 B2 | 3/2004 | Callol et al. |
| 6,712,827 B2 | 3/2004 | Ellis et al. |
| 6,712,845 B2 | 3/2004 | Hossainy |
| 6,723,071 B2 | 4/2004 | Gerdts et al. |
| 6,736,842 B2 | 5/2004 | Healy et al. |
| 6,743,219 B1 | 6/2004 | Dwyer et al. |
| 6,743,251 B1 | 6/2004 | Eder |
| 6,761,734 B2 | 7/2004 | Suhr |
| 6,776,771 B2 | 8/2004 | van Moorlegem et al. |
| 6,778,316 B2 | 8/2004 | Halas et al. |
| 6,790,227 B2 * | 9/2004 | Burgermeister ............. 623/1.15 |
| 6,800,065 B2 | 10/2004 | Duane et al. |
| 6,825,203 B2 | 11/2004 | Pasternak et al. |
| 6,837,901 B2 | 1/2005 | Rabkin et al. |
| 6,849,084 B2 | 2/2005 | Rabkin et al. |
| 6,852,252 B2 | 2/2005 | Halas et al. |
| 6,855,125 B2 | 2/2005 | Shanley |
| 6,858,034 B1 | 2/2005 | Hijlkema et al. |
| 6,878,161 B2 | 4/2005 | Lenker |
| 6,884,257 B1 | 4/2005 | Cox |

(56) References Cited

U.S. PATENT DOCUMENTS

| | | | |
|---|---|---|---|
| 6,893,417 B2 | 5/2005 | Gribbons et al. |
| 6,896,695 B2 | 5/2005 | Mueller et al. |
| 6,899,728 B1 | 5/2005 | Phillips et al. |
| 6,908,624 B2 | 6/2005 | Hossainy et al. |
| 6,913,619 B2 | 7/2005 | Brown et al. |
| 6,918,928 B2 | 7/2005 | Wolinsky et al. |
| 6,939,376 B2 | 9/2005 | Shulz et al. |
| 6,945,989 B1 | 9/2005 | Betelia et al. |
| 6,945,995 B2 | 9/2005 | Nicholas |
| 6,951,053 B2 | 10/2005 | Padilla et al. |
| 6,962,603 B1 | 11/2005 | Brown et al. |
| 6,964,676 B1 | 11/2005 | Gerberding et al. |
| 6,991,646 B2 | 1/2006 | Clerc et al. |
| 6,994,721 B2 | 2/2006 | Israel |
| 7,004,964 B2 | 2/2006 | Thompson et al. |
| 7,005,454 B2 | 2/2006 | Brocchini et al. |
| 7,022,132 B2 | 4/2006 | Kocur |
| 7,029,493 B2 | 4/2006 | Majercak et al. |
| 7,037,327 B2 | 5/2006 | Salmon et al. |
| 7,090,694 B1 | 8/2006 | Morris et al. |
| 7,101,840 B2 | 9/2006 | Brocchini et al. |
| 7,131,993 B2 * | 11/2006 | Gregorich | 623/1.16 |
| 7,137,993 B2 | 11/2006 | Acosta et al. |
| 7,141,063 B2 | 11/2006 | White et al. |
| 7,147,655 B2 | 12/2006 | Chermoni |
| 7,147,656 B2 | 12/2006 | Andreas et al. |
| 7,169,172 B2 | 1/2007 | Levine et al. |
| 7,169,174 B2 * | 1/2007 | Fischell et al. | 623/1.15 |
| 7,172,620 B2 | 2/2007 | Gilson |
| 7,175,654 B2 * | 2/2007 | Bonsignore et al. | 623/1.15 |
| 7,182,779 B2 | 2/2007 | Acosta et al. |
| 7,192,440 B2 | 3/2007 | Andreas et al. |
| 7,208,001 B2 | 4/2007 | Coyle et al. |
| 7,208,002 B2 | 4/2007 | Shelso |
| 7,220,755 B2 | 5/2007 | Betts et al. |
| 7,223,283 B2 * | 5/2007 | Chouinard | 623/1.15 |
| 7,238,197 B2 | 7/2007 | Sequin et al. |
| 7,241,308 B2 | 7/2007 | Andreas et al. |
| 7,244,336 B2 | 7/2007 | Fischer et al. |
| 7,270,668 B2 | 9/2007 | Andreas et al. |
| 7,294,146 B2 | 11/2007 | Chew et al. |
| 7,300,456 B2 | 11/2007 | Andreas et al. |
| 7,309,350 B2 | 12/2007 | Landreville et al. |
| 7,314,480 B2 | 1/2008 | Eidenschink et al. |
| 7,320,702 B2 | 1/2008 | Hammersmark et al. |
| 7,323,006 B2 | 1/2008 | Andreas et al. |
| 7,326,236 B2 | 2/2008 | Andreas et al. |
| 7,351,255 B2 | 4/2008 | Andreas |
| 7,402,168 B2 | 7/2008 | Sanderson et al. |
| 7,534,449 B2 | 5/2009 | Saltzman et al. |
| 7,699,886 B2 | 4/2010 | Sugimoto |
| 7,824,439 B2 * | 11/2010 | Toyokawa | 623/1.16 |
| 7,892,273 B2 | 2/2011 | George et al. |
| 7,892,274 B2 | 2/2011 | Will et al. |
| 7,905,913 B2 | 3/2011 | Chew et al. |
| 7,918,881 B2 | 4/2011 | Andreas et al. |
| 7,922,755 B2 | 4/2011 | Acosta et al. |
| 7,938,851 B2 | 5/2011 | Olson et al. |
| 7,938,852 B2 | 5/2011 | Andreas et al. |
| 7,993,388 B2 * | 8/2011 | Lee et al. | 623/1.15 |
| 8,016,870 B2 | 9/2011 | Chew et al. |
| 8,070,789 B2 | 12/2011 | Will et al. |
| 8,070,794 B2 * | 12/2011 | Issenmann | 623/1.15 |
| 8,157,851 B2 | 4/2012 | Andreas |
| 8,257,427 B2 | 9/2012 | Andersen et al. |
| 8,282,680 B2 | 10/2012 | Kao et al. |
| 8,317,850 B2 | 11/2012 | Kusleika |
| 8,317,859 B2 | 11/2012 | Snow et al. |
| 8,460,358 B2 | 6/2013 | Andreas et al. |
| 8,486,132 B2 | 7/2013 | Snow et al. |
| 8,585,747 B2 | 11/2013 | Andreas et al. |
| 8,702,781 B2 | 4/2014 | Acosta et al. |
| 8,740,968 B2 | 6/2014 | Kao et al. |
| 2001/0001824 A1 | 5/2001 | Wu |
| 2001/0020154 A1 | 9/2001 | Bigus et al. |
| 2001/0020173 A1 | 9/2001 | Klumb et al. |
| 2001/0020181 A1 | 9/2001 | Layne |
| 2001/0035902 A1 | 11/2001 | Iddan et al. |
| 2001/0044595 A1 | 11/2001 | Reydel et al. |
| 2001/0044632 A1 | 11/2001 | Daniel et al. |
| 2001/0049547 A1 | 12/2001 | Moore |
| 2001/0049549 A1 | 12/2001 | Boylan et al. |
| 2002/0007212 A1 * | 1/2002 | Brown et al. | 623/1.16 |
| 2002/0032457 A1 | 3/2002 | Sirhan et al. |
| 2002/0035395 A1 | 3/2002 | Sugimoto |
| 2002/0037358 A1 | 3/2002 | Barry et al. |
| 2002/0045914 A1 | 4/2002 | Roberts et al. |
| 2002/0052642 A1 | 5/2002 | Cox et al. |
| 2002/0087186 A1 | 7/2002 | Shelso |
| 2002/0091439 A1 | 7/2002 | Baker et al. |
| 2002/0092536 A1 | 7/2002 | LaFontaine et al. |
| 2002/0107560 A1 | 8/2002 | Richter |
| 2002/0111671 A1 | 8/2002 | Stenzel |
| 2002/0123786 A1 | 9/2002 | Gittings et al. |
| 2002/0123792 A1 | 9/2002 | Burgermeister |
| 2002/0128706 A1 | 9/2002 | Osypka |
| 2002/0138132 A1 | 9/2002 | Brown |
| 2002/0151924 A1 | 10/2002 | Shiber |
| 2002/0151955 A1 | 10/2002 | Tran et al. |
| 2002/0156496 A1 | 10/2002 | Chermoni |
| 2002/0165599 A1 | 11/2002 | Nasralla |
| 2002/0168317 A1 | 11/2002 | Daighighian et al. |
| 2002/0177890 A1 | 11/2002 | Lenker |
| 2002/0183763 A1 | 12/2002 | Callol et al. |
| 2002/0188343 A1 | 12/2002 | Mathis |
| 2002/0188347 A1 | 12/2002 | Mathis |
| 2002/0193873 A1 | 12/2002 | Brucker et al. |
| 2003/0013266 A1 | 1/2003 | Fukuda et al. |
| 2003/0045923 A1 | 3/2003 | Bashiri et al. |
| 2003/0093143 A1 | 5/2003 | Zhao et al. |
| 2003/0097169 A1 | 5/2003 | Brucker et al. |
| 2003/0105511 A1 * | 6/2003 | Welsh et al. | 623/1.15 |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0125800 A1 | 7/2003 | Shulze et al. |
| 2003/0125802 A1 | 7/2003 | Callol et al. |
| 2003/0135259 A1 | 7/2003 | Simso |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0139798 A1 | 7/2003 | Brown et al. |
| 2003/0163085 A1 | 8/2003 | Tanner et al. |
| 2003/0163155 A1 | 8/2003 | Haverkost et al. |
| 2003/0176909 A1 | 9/2003 | Kusleika |
| 2003/0191516 A1 | 10/2003 | Weldon et al. |
| 2003/0195609 A1 | 10/2003 | Berenstein |
| 2003/0199821 A1 | 10/2003 | Gerdts et al. |
| 2003/0204238 A1 | 10/2003 | Tedeschi |
| 2003/0208223 A1 | 11/2003 | Kleiner |
| 2003/0212447 A1 | 11/2003 | Euteneuer et al. |
| 2003/0225446 A1 | 12/2003 | Hartley |
| 2004/0015224 A1 | 1/2004 | Armstrong et al. |
| 2004/0024450 A1 | 2/2004 | Shulze et al. |
| 2004/0030380 A1 | 2/2004 | Shulze et al. |
| 2004/0044395 A1 | 3/2004 | Nelson |
| 2004/0047909 A1 | 3/2004 | Ragheb et al. |
| 2004/0073290 A1 | 4/2004 | Chouinard |
| 2004/0087965 A1 | 5/2004 | Levine et al. |
| 2004/0088044 A1 * | 5/2004 | Brown et al. | 623/1.16 |
| 2004/0093061 A1 | 5/2004 | Acosta et al. |
| 2004/0093067 A1 | 5/2004 | Israel |
| 2004/0093077 A1 | 5/2004 | White et al. |
| 2004/0098081 A1 | 5/2004 | Landreville et al. |
| 2004/0106979 A1 | 6/2004 | Goicoechea |
| 2004/0111145 A1 | 6/2004 | Serino et al. |
| 2004/0117008 A1 | 6/2004 | Wnendt et al. |
| 2004/0138737 A1 * | 7/2004 | Davidson et al. | 623/1.35 |
| 2004/0143322 A1 | 7/2004 | Litvack et al. |
| 2004/0176832 A1 | 9/2004 | Hartley et al. |
| 2004/0181239 A1 | 9/2004 | Dorn et al. |
| 2004/0186551 A1 | 9/2004 | Kao et al. |
| 2004/0193245 A1 | 9/2004 | Deem et al. |

(56) References Cited

U.S. PATENT DOCUMENTS

| | | |
|---|---|---|
| 2004/0215165 A1 | 10/2004 | Coyle et al. |
| 2004/0215312 A1 | 10/2004 | Andreas et al. |
| 2004/0215331 A1 | 10/2004 | Chew et al. |
| 2004/0230285 A1 | 11/2004 | Gifford, III et al. |
| 2004/0243217 A1 | 12/2004 | Andersen et al. |
| 2004/0249434 A1 | 12/2004 | Andreas et al. |
| 2004/0249435 A1 | 12/2004 | Andreas et al. |
| 2004/0249439 A1 | 12/2004 | Richter et al. |
| 2005/0004657 A1* | 1/2005 | Burgermeister ............. 623/1.16 |
| 2005/0010276 A1 | 1/2005 | Acosta et al. |
| 2005/0038494 A1 | 2/2005 | Eidenschink |
| 2005/0038505 A1 | 2/2005 | Shulze et al. |
| 2005/0049673 A1 | 3/2005 | Andreas et al. |
| 2005/0055077 A1 | 3/2005 | Marco et al. |
| 2005/0075716 A1* | 4/2005 | Yan ............................ 623/1.15 |
| 2005/0080474 A1 | 4/2005 | Andreas et al. |
| 2005/0080475 A1 | 4/2005 | Andreas et al. |
| 2005/0085897 A1 | 4/2005 | Bonsignore |
| 2005/0090846 A1 | 4/2005 | Pedersen et al. |
| 2005/0101624 A1 | 5/2005 | Betts et al. |
| 2005/0123451 A1 | 6/2005 | Nomura |
| 2005/0125051 A1 | 6/2005 | Eidenschink et al. |
| 2005/0131008 A1 | 6/2005 | Betts et al. |
| 2005/0133164 A1 | 6/2005 | Fischer et al. |
| 2005/0137622 A1 | 6/2005 | Griffin |
| 2005/0143827 A1 | 6/2005 | Globerman et al. |
| 2005/0149159 A1 | 7/2005 | Andreas et al. |
| 2005/0149168 A1* | 7/2005 | Gregorich ................... 623/1.15 |
| 2005/0165378 A1 | 7/2005 | Heinrich et al. |
| 2005/0171568 A1 | 8/2005 | Duffy |
| 2005/0182477 A1 | 8/2005 | White |
| 2005/0209674 A1 | 9/2005 | Kutscher et al. |
| 2005/0209676 A1 | 9/2005 | Kusleika |
| 2005/0209680 A1 | 9/2005 | Gale et al. |
| 2005/0222671 A1 | 10/2005 | Schaeffer et al. |
| 2005/0228477 A1 | 10/2005 | Grainger et al. |
| 2005/0245637 A1 | 11/2005 | Hossainy et al. |
| 2005/0249777 A1 | 11/2005 | Michal et al. |
| 2005/0278011 A1 | 12/2005 | Peckham |
| 2005/0288763 A1 | 12/2005 | Andreas et al. |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0173529 A1 | 8/2006 | Blank |
| 2006/0177476 A1 | 8/2006 | Saffran |
| 2006/0200223 A1 | 9/2006 | Andreas et al. |
| 2006/0206190 A1 | 9/2006 | Chermoni |
| 2006/0229700 A1 | 10/2006 | Acosta et al. |
| 2006/0229706 A1 | 10/2006 | Shulze et al. |
| 2006/0271150 A1 | 11/2006 | Andreas et al. |
| 2006/0271151 A1 | 11/2006 | McGarry et al. |
| 2006/0282147 A1 | 12/2006 | Andreas et al. |
| 2006/0282149 A1 | 12/2006 | Kao |
| 2006/0282150 A1 | 12/2006 | Olson et al. |
| 2006/0287726 A1 | 12/2006 | Segal et al. |
| 2007/0010869 A1* | 1/2007 | Sano ........................... 623/1.15 |
| 2007/0027521 A1 | 2/2007 | Andreas et al. |
| 2007/0043419 A1 | 2/2007 | Nikolchev et al. |
| 2007/0067012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |
| 2007/0100423 A1 | 5/2007 | Acosta et al. |
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0129733 A1 | 6/2007 | Will et al. |
| 2007/0135906 A1 | 6/2007 | Badylak et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0219612 A1 | 9/2007 | Andreas et al. |
| 2007/0219613 A1 | 9/2007 | Kao et al. |
| 2007/0265637 A1 | 11/2007 | Andreas et al. |
| 2007/0270936 A1 | 11/2007 | Andreas et al. |
| 2007/0276461 A1 | 11/2007 | Andreas et al. |
| 2007/0281117 A1 | 12/2007 | Kaplan et al. |
| 2007/0292518 A1 | 12/2007 | Ludwig |
| 2008/0004690 A1 | 1/2008 | Robaina |
| 2008/0046067 A1 | 2/2008 | Toyokawa |
| 2008/0071345 A1 | 3/2008 | Hammersmark et al. |
| 2008/0077229 A1 | 3/2008 | Andreas et al. |
| 2008/0091257 A1 | 4/2008 | Andreas et al. |
| 2008/0097574 A1 | 4/2008 | Andreas et al. |
| 2008/0125850 A1 | 5/2008 | Andreas et al. |
| 2008/0132989 A1 | 6/2008 | Snow et al. |
| 2008/0147162 A1 | 6/2008 | Andreas et al. |
| 2008/0177369 A1 | 7/2008 | Will et al. |
| 2008/0199510 A1 | 8/2008 | Ruane et al. |
| 2008/0208311 A1 | 8/2008 | Kao et al. |
| 2008/0208318 A1 | 8/2008 | Kao et al. |
| 2008/0234795 A1 | 9/2008 | Snow et al. |
| 2008/0234798 A1 | 9/2008 | Chew et al. |
| 2008/0234799 A1 | 9/2008 | Acosiya et al. |
| 2008/0243225 A1 | 10/2008 | Satasiya et al. |
| 2008/0249607 A1 | 10/2008 | Webster et al. |
| 2008/0269865 A1 | 10/2008 | Snow et al. |
| 2009/0076584 A1 | 3/2009 | Mao et al. |
| 2009/0088832 A1 | 4/2009 | Chew et al. |
| 2009/0105686 A1 | 4/2009 | Snow et al. |
| 2009/0149863 A1 | 6/2009 | Andreas et al. |
| 2009/0234428 A1 | 9/2009 | Snow et al. |
| 2009/0248137 A1 | 10/2009 | Andersen et al. |
| 2009/0248140 A1* | 10/2009 | Gerberding ................. 623/1.18 |
| 2009/0264979 A1 | 10/2009 | Kao et al. |
| 2009/0276030 A1 | 11/2009 | Kusleika |
| 2010/0004729 A1 | 1/2010 | Chew et al. |
| 2011/0022148 A1 | 1/2011 | Ruane et al. |
| 2011/0093056 A1 | 4/2011 | Kaplan et al. |
| 2011/0125248 A1 | 5/2011 | George et al. |
| 2011/0152996 A1 | 6/2011 | Snow et al. |
| 2013/0060321 A1 | 3/2013 | Kao et al. |
| 2013/0211494 A1 | 8/2013 | Snow et al. |
| 2014/0018899 A1 | 1/2014 | Snow et al. |
| 2014/0188205 A1 | 7/2014 | Andreas et al. |
| 2014/0228931 A1 | 8/2014 | Acosta et al. |
| 2014/0236282 A1 | 8/2014 | Andreas et al. |

FOREIGN PATENT DOCUMENTS

| | | |
|---|---|---|
| DE | 1 963 0469 | 1/1998 |
| DE | 199 50 756 | 8/2000 |
| DE | 101 03 000 | 8/2002 |
| EP | 0 203 945 B2 | 12/1986 |
| EP | 0 274 129 B1 | 7/1988 |
| EP | 0 282 143 | 9/1988 |
| EP | 0 364 787 A1 | 4/1990 |
| EP | 0 505 686 | 9/1992 |
| EP | 0 533 960 | 3/1993 |
| EP | 0 696 447 A2 | 2/1996 |
| EP | 0 714 640 | 6/1996 |
| EP | 0 797 963 A2 | 1/1997 |
| EP | 0 596 145 | 5/1997 |
| EP | 0 947 180 | 10/1999 |
| EP | 1 254 644 A1 | 11/2002 |
| EP | 1 258 230 | 11/2002 |
| EP | 1 266 638 B1 | 12/2002 |
| EP | 1 277 449 | 1/2003 |
| EP | 1 290 987 A2 | 3/2003 |
| EP | 1 318 765 | 6/2003 |
| EP | 1 470 834 | 10/2004 |
| EP | 1 523 959 A2 | 4/2005 |
| EP | 1 523 960 A2 | 4/2005 |
| EP | 1 743 603 A2 | 1/2007 |
| GB | 2277875 A | 11/1994 |
| JP | 03-133446 | 6/1991 |
| JP | 07-132147 | 5/1995 |
| JP | 10-503663 | 4/1998 |
| JP | 10-295823 | 11/1998 |
| JP | 11-503056 T | 3/1999 |
| JP | 2935561 B2 | 8/1999 |
| JP | 2001-190687 | 7/2001 |

(56) References Cited

FOREIGN PATENT DOCUMENTS

| | | |
|---|---|---|
| JP | 2002-538932 T | 11/2002 |
| JP | 2004-121343 A | 4/2004 |
| WO | 94/27667 A1 | 12/1994 |
| WO | 95/26695 A2 | 10/1995 |
| WO | WO 95/29647 | 11/1995 |
| WO | WO 96/26689 | 9/1996 |
| WO | WO 96/33677 | 10/1996 |
| WO | 96/37167 A1 | 11/1996 |
| WO | 96/39077 A1 | 12/1996 |
| WO | 97/10778 | 3/1997 |
| WO | WO 97/46174 | 12/1997 |
| WO | WO 97/48351 | 12/1997 |
| WO | WO 98/20810 | 5/1998 |
| WO | WO 98/37833 | 9/1998 |
| WO | WO 98/58600 | 12/1998 |
| WO | WO 99/01087 | 1/1999 |
| WO | 99/65421 | 12/1999 |
| WO | WO 00/12832 A3 | 3/2000 |
| WO | WO 00/15151 | 3/2000 |
| WO | WO 00/25841 | 5/2000 |
| WO | WO 00/32136 | 6/2000 |
| WO | WO 00/41649 | 7/2000 |
| WO | WO 00/50116 | 8/2000 |
| WO | 00/51525 A1 | 9/2000 |
| WO | 00/56237 A2 | 9/2000 |
| WO | WO 00/62708 | 10/2000 |
| WO | WO 00/72780 | 12/2000 |
| WO | 01/26707 | 4/2001 |
| WO | 01/34063 | 5/2001 |
| WO | WO 01/70297 | 9/2001 |
| WO | WO 01/91918 | 12/2001 |
| WO | 02/060344 | 8/2002 |
| WO | 02/071975 | 9/2002 |
| WO | WO 02/085253 | 10/2002 |
| WO | 02/098326 A1 | 12/2002 |
| WO | WO 03/022178 | 3/2003 |
| WO | WO 03/047651 | 6/2003 |
| WO | WO 03/051425 | 6/2003 |
| WO | WO 03/075797 | 9/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 A2 | 6/2004 |
| WO | 2004/087006 | 10/2004 |
| WO | 2004/091441 | 10/2004 |
| WO | WO 2005/009295 | 2/2005 |
| WO | WO 2005/013853 | 2/2005 |
| WO | 2005/023153 | 3/2005 |
| WO | WO 2006/036939 | 4/2006 |
| WO | WO 2006/047520 | 5/2006 |
| WO | WO 2007/035805 | 3/2007 |
| WO | WO 2007/053187 | 5/2007 |
| WO | WO 2007/146411 | 12/2007 |
| WO | WO 2008/005111 | 1/2008 |
| WO | 2009/0111203 A2 | 9/2009 |

OTHER PUBLICATIONS

"Drug Delivery Stent With Holes Located on Neutral Axis" Research Disclosure, Kenneth Mason Publications, Hampshire, CB, No. 429, Jan. 2000, p. 13, XP00976354.

Chu et al., "Preparation of Thermo-Responsive Core-Shell Microcapsules with a Porous Membrane and Poly(N-isopropylacrylamide) Gates," J Membrane Sci, Oct. 15, 2001; 192(1-2):27-39.

Tilley , "Biolimus A9-Eluting Stent Shows Promise," Medscape Medical News, Oct. 5, 2004; retrieved from the internet: <http://www.medscape.com/viewarticle/490621>, 2 pages total.

Weir et al., "Degradation of poly-L-lactide. Part 2: increased temperature accelerated degradation," Proc Inst Mech Eng H. 2004;218(5):321-30.

Extended European Search Report of corresponding European Application No. 09717057.5, dated Feb. 15, 2013. 5 pages.

Supplementary European Search Report of EP Patent Application No. 07758831, dated Dec. 14, 2009.

International Search Report and Written Opinion of PCT Application No. PCT/US2007/086864, mailed May 13, 2008, 13 pages total.

Supplementary European Search Report of EP Patent Application No. 02804509, dated Dec. 13, 2006, 2 pages total.

Supplementary European Search Report of EP Patent Application No. 04749567, dated Sep. 11, 2006, 2 pages total.

International Search Report and Written Opinion of PCT Application No. PCT/US2008/061041, mailed Nov. 7, 2008, 13 pages total.

The State Intellectual Property Office of the Republic of China, Application No. 200880100150.2, First Office Action date of dispatch Oct. 26, 2011, 11 pages.

The State Intellectual Property Office of the People's Republic of China, Application No. 200880100150.2, Second Office Action date of dispatch Jul. 25, 2012, 23 pages.

Office Action of Japanese Patent Application No. 2006-547139, mailed Jun. 15, 2010, 5 pages total. (English translation included).

The State Intellectual Property Office of the People's Republic of China, 200880100150.2, Third Office Action date of dispatch Apr. 12, 2013, 26 pages.

Colombo, "The Invatec Bifurcation Stent Solution" Bifurcation Stents: Novel Solutions, TCT 2003, Washington: Sep. 15-19, 2003, 24 pages total.

Cooley et al., "Applications of Ink-Jet Printing Technology to BioMEMs and Microfluidic Systems," Proceedings, SPIE Conference on Microfludics and BioMEMs, (Oct. 2001).

Evans Analytical Group, "Functional Sites on Non-polymeric Materials: Gas Plasma Treatment and Surface Analysis," http://www.eaglabs.com.

Joung et al., "Estrogen Release from metallic Stent Surface for the Prevention of Restenosis," Journal of Controlled Release 92 (2003) pp. 83-91.

Lefevre et al. "Approach to Coronary Bifurcation Stenting in 2003," Euro PCR, (May 2003) 28 pages total.

"STENT". Definitions from Dictionary.com. Unabridged 9v1.01). Retrieved Sep. 22, 2006, from Dictionary.com website: <http://dictionary.reference.com/search?q=stent>.

Stimpson et al., Parallel Production of Oligonucleotide Arrays using Membranes and Reagent Jet Printing, BioTechniques 25:886-890 (Nov. 1998).

Supplementary European Search Report of EP patent Application No. 05727731.1, dated Mar. 25, 2008, 2 pages total.

Supplementary European Search Report of EP Patent Application No. 05744136, dated Mar. 26, 2008, 3 pages total.

U.S. Appl. No. 60/336,607, filed Dec. 3, 2001, first names inventor: Bernard Andreas.

U.S. Appl. No. 60/336,767, filed Dec. 3, 2001, first named inventor: Bernard Andreas.

U.S. Appl. No. 60/336,967, filed Dec. 3, 2001, first named inventor: Sunmi Chew.

U.S. Appl. No. 60/364,389, filed Mar. 13, 2002, first named inventor: Sunmi Chew.

U.S. Appl. No. 60/440,839, filed Jan. 17, 2003, first named inventor: Bernard Andreas.

U.S. Appl. No. 60/561,041, filed Apr. 9, 2004, first named inventor: Jeffry Grainger.

U.S. Appl. No. 60/784,309, filed Mar. 20, 2006, first named inventor: Bernard Andreas.

U.S. Appl. No. 60/810,522, filed Jun. 2, 2006, first named inventor: Stephen Kaplan.

U.S. Appl. No. 60/890,703, filed Feb. 20, 2007, first named inventor: Patrick Ruane.

U.S. Appl. No. 61/012,317, filed Dec. 7, 2007, first named inventor: Patrick Ruane.

U.S. Appl. No. 09/097,855, filed Jun. 15, 1998, first named inventor: Enrique J. Klein; Abandoned.

U.S. Appl. No. 09/225,364, filed Jan. 4, 1999, first named inventor: Aaron V. Kaplan; abandoned.

U.S. Appl. No. 10/874,859, filed Jun. 22, 2004, first named inventor: Pablo Acosta. Abandoned.

U.S. Appl. No. 11/462,951, filed Aug. 7, 2006, first named inventor: David Snow.

(56) References Cited

OTHER PUBLICATIONS

U.S. Appl. No. 11/627,096, filed Jan. 25, 2007, first named inventor: Bernard Andreas.
U.S. Appl. No. 11/689,927, filed Mar. 22, 2007, first named inventor: David Snow.
U.S. Appl. No. 11/752,448, filed May 23, 2007, first named inventor: David Snow.
U.S. Appl. No. 11/771,929, filed Jun. 29, 2007, first named inventor: David Snow.
U.S. Appl. No. 11/857,562, filed Sep. 19, 2007, first named inventor: Bryan Mao.
U.S. Appl. No. 11/938,730, filed Nov. 12, 2007, first named inventor: Sunmi Chew.
U.S. Appl. No. 11/945,142, filed Nov. 26, 2007, first named inventor: Bernard Andreas.
U.S. Appl. No. 11/947,677, filed Nov. 29, 2007, first named inventor: Dan Hammersmark.
U.S. Appl. No. 11/952,644, filed Dec. 7, 2007, first named inventor: Bernard Andreas.
U.S. Appl. No. 12/033,586, filed Feb. 19, 2008, first named inventor: Patrick H. Ruane.
U.S. Appl. No. 12/040,598, filed Feb. 29, 2008, first named inventor: Bernard Andreas.
U.S. Appl. No. 12/061,951, filed Apr. 3, 2008, first named inventor: Stephen Kao.
U.S. Appl. No. 12/109,477, filed Apr. 25, 2008, first named inventor: Stephen Kao.
U.S. Appl. No. 12/127,147, filed May 27, 2008, first named inventor: Sunmi Chew.
U.S. Appl. No. 12/133,909, filed Jun. 5, 2008, first named inventor: David Sanderson.

\* cited by examiner

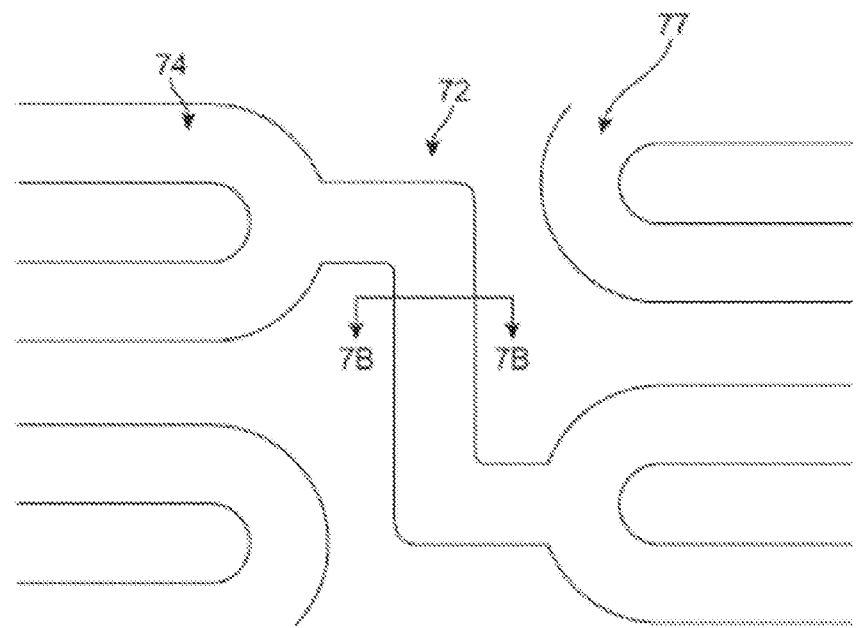
FIG. 7A
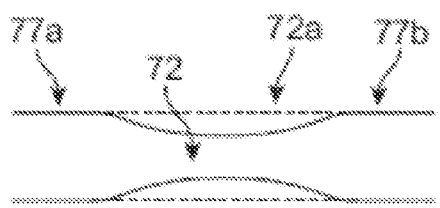 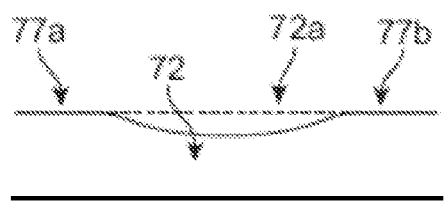
FIG. 7B-1     FIG. 7B-2
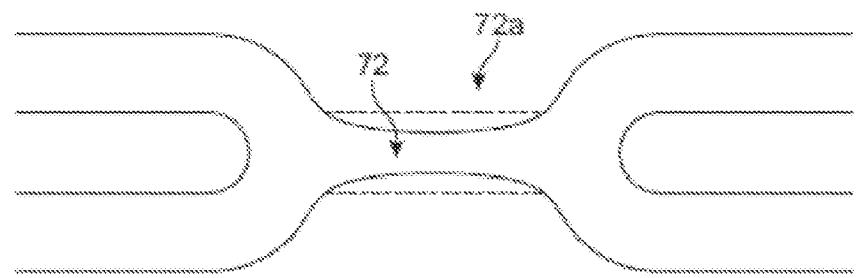
FIG. 7C

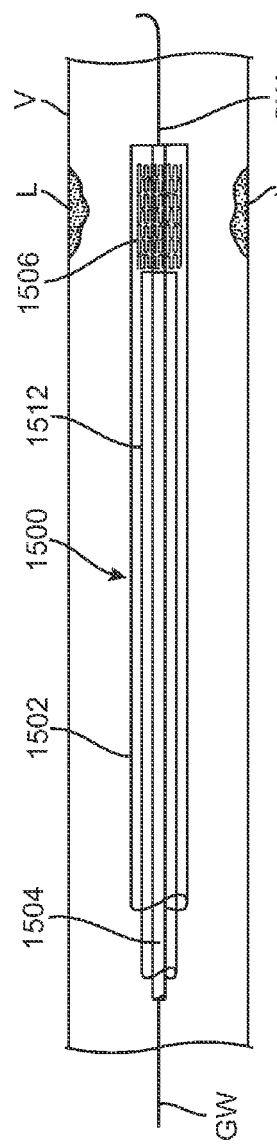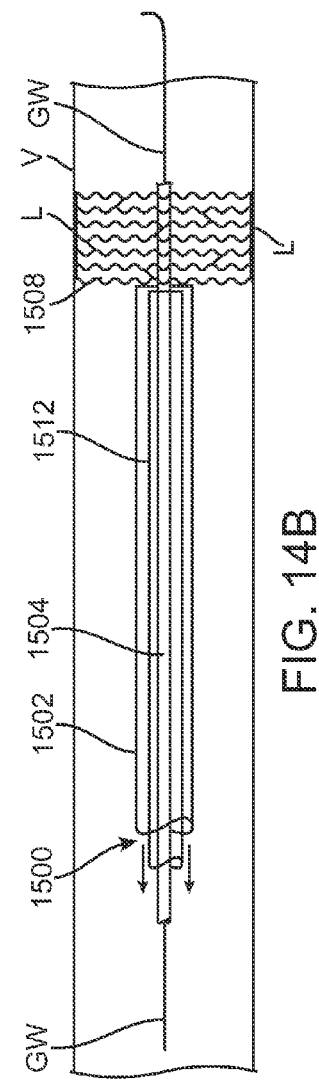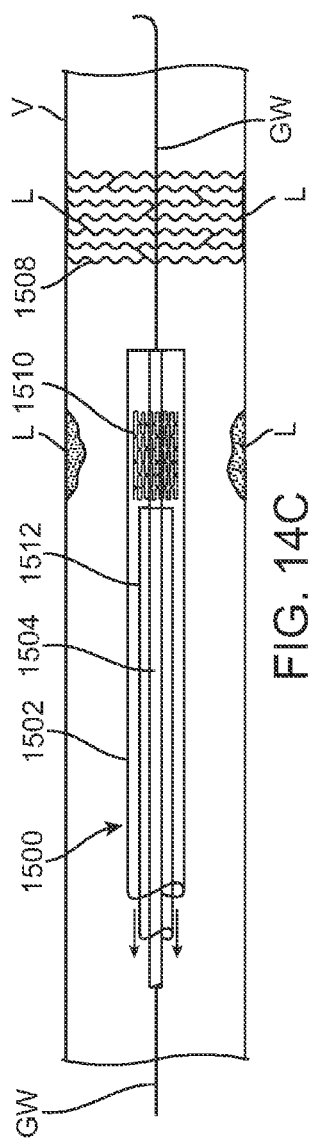

APPARATUS HAVING VARIABLE STRUT LENGTH AND METHODS OF USE

CROSS-REFERENCES TO RELATED APPLICATIONS

Not Applicable

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

1. Field of Invention

The invention generally relates to medical apparatus and methods, and more specifically to prosthetic devices such as stents for use in the coronary and peripheral arteries as well as in other vessels and body lumens.

Stenting is an important treatment for patients with vascular occlusive disease. A stent is often a hollow, tubular implant designed to provide scaffolding to the walls of a diseased blood vessel or other body lumen in order to maintain patency of the vessel or lumen. Stents are usually placed at the site of a stenotic lesion within an artery after a primary treatment such as angioplasty. They are typically delivered to the arteries using long, flexible catheters inserted percutaneously through the patient's femoral artery.

Stents are typically either balloon expandable or self-expandable. Balloon expandable stents are mounted over a balloon or other expansion element on a delivery catheter. When the balloon is inflated, the balloon expands and correspondingly expands and deforms the stent to a desired diameter. The balloon can then be deflated and removed, leaving the stent in place.

A self-expanding stent is simply released from the delivery catheter so that it expands until it engages the vessel wall. Self-expanding stents are typically delivered to a treatment site while compressed or crimped within a constraining sheath. Retraction of the sheath removes the constraint and allows the stent to radially expand into engagement with the vessel wall.

Self-expanding stents may be made of materials having high elasticity or a shape memory alloy such as Nitinol, a nickel-titanium (NiTi) alloy. Resilient, self-expanding stents are often used in the peripheral vascular system and regions of the body closer to the body's surface because their resilience helps minimize damage or crushing caused by body movement or externally applied forces.

Self-expanding stents may also have certain advantages over balloon expandable stents in the treatment of arteries. Balloon expandable stents are often expanded to a constant diameter and do not conform well with an artery having variations in diameter due to vessel tortuosity or taper. Because of the potential mismatch between stent diameter and vessel diameter, there is a possibility for gaps to form between the outer stent surface and the inner vessel wall, and this can lead to thrombosis formation. Self-expanding stents expand until their outer surface is constrained by contact with the vessel wall and thus the use of a self-expanding stent may eliminate or reduce these gaps thereby reducing thrombosis formation.

Another trend in stenting is the use of longer stents for treatment of long diffuse lesions in the peripheral vessels. While this procedure is promising, some challenges still exist. For example, longer stents are often less flexible and therefore are harder to deliver and deploy in torturous vessels, and they can fracture or kink. Therefore, there is a need for longer stents with improved flexibility.

The flexibility of stents may be improved through the variation of the stent geometry. Current stents are typically articulated tubes consisting of a series of axially adjacent, tubular rings interconnected with one another by one or more bridges. Each tubular ring often consists of several repeating cells formed from axially oriented struts, each having the same length. The cells are often arranged to form a helical, zig-zag, diamond, rectangular, undulating, mesh, or other pattern. Using struts of the same length in a repeating cell pattern results in uniform stent compression and expansion thereby helping to ensure uniform loading of a stent with a delivery catheter as well as uniform scaffolding of the treatment site after the stent has been deployed. The tubular rings are often rigid, providing mechanical support to the vessel but little or no axial flexibility. Thus, axial flexibility of the stent may be adjusted by using bridges to connect adjacent tubular rings. While it is desirable to keep the tubular rings close together in order to provide maximum scaffolding to the vessel, it is also desirable to have a longer gap between the tubular rings so that a longer bridge may connect adjacent tubular rings for greater stent flexibility. Additionally, by bringing tubular rings closer together or interleaving segment ends, the overall stent column strength is increased along with the stent's ability to resist twisting. This allows the stent rings to be coupled together with fewer bridges, thereby also increasing stent flexibility. Stent column strength is important during retraction of a constraining sheath during stent deployment. Friction between the sheath and the tubular rings may twist them relative to one another or buckle the stent forcing the segments together, thereby causing binding or potentially interfering with proper stent deployment. Thus, it is desirable to provide an improved stent that provides improved flexibility without substantially diminishing scaffolding ability or column strength, as well as providing other structural advantages while avoiding some of the aforementioned challenges.

2. Description of the Background Art

Prior patents and publications describing various stent geometries and stent delivery systems include U.S. Pat. Nos. 5,421,955; 5,716,393; 6,022,374; 6,132,460; 6,264,688; 6,273,911; 6,334,871; 6,375,676; 6,464,720; 6,582,460; 6,918,928; U.S. Patent Publication No. 2003/0114919; International PCT Publication WO 2008/005111; and European Patent No. EP 1318765.

BRIEF SUMMARY OF THE INVENTION

The present invention provides prostheses and methods for use thereof. In a first aspect of the present invention, a tubular prosthesis comprises a plurality of tubular rings radially expandable from a contracted configuration to an expanded configuration. Each ring has a plurality of axially oriented struts interconnected so as to form a circumferential series of at least one high peak and at least one low peak. The high and low peaks have apices that are oriented in the same axial direction and the apices of the high peaks are also axially offset from the apices of the low peaks. A bridge member couples a pair of adjacent tubular rings together and the bridge member has a first end connected to a first low peak in a first tubular ring and a second end connected to either a high or low peak in an adjacent tubular ring.

In another aspect of the present invention, a tubular prosthesis comprises a plurality of tubular rings radially expandable from a contracted configuration to an expanded configuration. Each ring comprises a plurality of axially oriented struts interconnected so as to form a circumferential series of high peaks and low peaks, the high and low peaks having apices oriented in the same axial direction and the apices of the high peaks are axially offset from the apices of the low peaks. Adjacent tubular rings interleave with one another such that a high peak on a first tubular ring nests between two high peaks on an adjacent tubular ring. A bridge member couples a pair of adjacent tubular rings together and the bridge member has a first end connected to the first tubular ring and a second end connected to the adjacent tubular ring.

In yet another aspect of the present invention, a method for delivering a prosthesis to a treatment site in a body comprises advancing a delivery catheter to the treatment site. The delivery catheter has a tubular prosthesis disposed thereon and the tubular prosthesis comprises a plurality of tubular rings with each ring having a plurality of axially oriented struts interconnected so as to form a circumferential series of at last one high peak and at least one low peak. The apex of the at least one high peak is axially offset from the apex of the at least one low peak. The method also includes selecting a first number of the tubular rings for deployment and radially expanding the first number of tubular rings into engagement with tissue at the treatment site. The delivery catheter may be repositioned to a second treatment site and then a second number of the tubular rings may be selected for deployment. The second number of rings is radially expanded so that they engage with tissue at the second treatment site without removing the delivery catheter from the body.

Advancing the delivery catheter may include intravascularly positioning the catheter in a blood vessel which may be an artery in a leg. Sometimes the plurality of tubular rings are self-expanding and radially expanding the first number comprises removing a constraint from the first number and/or the second number of tubular rings. The method may also include releasing a therapeutic agent carried by the tubular prosthesis at a controlled rate, such as an agent that inhibits restenosis. The first number may be greater than or equal to two and the second number may be different than the first number.

The apices of the high and low peaks in the first tubular ring may be circumferentially offset from the apices of the high and low peaks in the adjacent tubular ring. The apices of the low peaks in the first tubular ring may be circumferentially aligned with the apices of the high or low peaks in the adjacent tubular ring. The apices of the high and low peaks of the first tubular ring may point toward the apices of the high and low peaks of the adjacent tubular ring. The high and low peaks may be circumferentially alternative with one another in a tubular ring or they may be arranged circumferentially such that each high peak is disposed between two low peaks or one low peak and one high peak. Each high and low peak may be separated from an adjacent high or low peak by a valley, and the high peaks on the first tubular ring may be nested between valleys on the adjacent tubular ring. The circumferential width of each valley in the contracted configuration may be less than the circumferential width of each peak in the contracted configuration. The first low peak may be circumferentially offset from the high or the low peak in the adjacent tubular ring.

The plurality of axially oriented struts may comprise long struts and short struts with the short struts being shorter than the long struts and the plurality of axially oriented struts may be arranged circumferentially such that each short strut is disposed between one long strut and one short strut. Each high peak may comprise a long strut having a first length and each low peak may comprise a short strut having a second length shorter than the first length. Each low peak may comprise two short struts and each high peak may comprise one long strut and one short strut with the short strut being shorter than the long strut.

Various embodiments of bridge members are disclosed including bridge members having a shape selected from the group consisting of z, u, and s-shaped as well as sigmoidal shaped. Sometimes the bridge member may have a surface defining one or more apertures therein and sometimes the apertures may extend entirely through the bridge member. The apertures may have an axis that is substantially parallel to an outer surface of the prosthesis and sometimes the apertures may form an elongate slot. The bridge member has a thickness in the radial direction and sometimes that thickness may vary across the bridge member. The bridge member may have a first thickness and the plurality of axially oriented struts may have a second thickness greater than or different than the first thickness. The first thickness may be less than the second thickness. Some bridge members may comprise a spring element, a strain relief region or a resilient elastomer. Sometimes the bridge member may be slidably engaged with the connector.

The bridge member may comprise a transverse portion and a first axially oriented portion with the transverse portion transverse to the first axially oriented portion and coupled thereto. The bridge member may also further comprise a second axially oriented portion with the transverse portion disposed between the first and second axially oriented portions. The bridge member may have an axial length between the first and second ends that is longer than the axial distance between high peaks on adjacent tubular rings, or the axial length may be longer than the axial distance between a high peak and a low peak on adjacent tubular rings. The first end may be connected to either a high or low peak in the first tubular ring and the second end may be connected to either a second high or low peak in the adjacent tubular ring. The first end of the bridge member may connect to either the apex of the peak or a portion of the peak offset from the peak's apex. The second end of the bridge member may also connect to a portion of a peak offset from the apex in the adjacent tubular ring.

The tubular prosthesis may have a first ring disposed between the adjacent tubular ring and a third tubular ring with the first tubular ring connected to the third tubular ring by a second bridge member. The bridge member may have a first orientation and the second bridge member may have a second orientation that is a mirror image thereof, or the bridge member may have a first slope and the second bridge member may have a second slope that is opposite of the first.

The first end of the bridge member may connect to the first low peak at its apex. The second end of the bridge member may connect to the apex of either a high or low peak in the adjacent tubular ring. The bridge member may comprise a transverse portion that is transversely oriented to a longitudinal axis of the tubular prosthesis. The transverse portion may be disposed between a first peak on the first tubular ring and a second peak on the adjacent tubular ring thereby preventing the first peak from overlapping with the second peak when the tubular prosthesis is in compression. The transverse portion may have a length greater than a circumferential distance between the first and second peaks. The bridge member may also comprise an axial portion and a circumferential portion that is substantially transverse thereto. The bridge member may have a width that is substantially equivalent to a width of the axial struts. The bridge member may also comprise a first axially oriented region which includes the first end and a second axially oriented region which includes the second end.

The tubular prosthesis may be self-expanding and may have a length in the range from about 2 mm to about 200 mm. Sometimes, each of the plurality of tubular rings may have substantially the same axial length or they may be different. The prosthesis may comprise a third tubular ring adjacent the first tubular ring but that is not connected thereto. The prosthesis may further comprise a fourth tubular ring that is unconnected to but deployable with the first or third tubular ring. The prosthesis may carry a therapeutic agent that can be released from the prosthesis at a controlled rate and that agent may inhibit restenosis.

These and other embodiments are described in further detail in the following description related to the appended drawing figures.

BRIEF DESCRIPTION OF THE DRAWINGS

FIG. 7A shows a bridge member having an arcuate surface.
FIG. 7B-1 and 7B-2 are cross-sectional views of the bridge member of FIG. 7A.
FIG. 7C shows a bridge member having a tapered region.
FIGS. 14A-14C illustrate an exemplary method of deploying a prosthesis.

DETAILED DESCRIPTION OF THE INVENTION

Figure 1A:
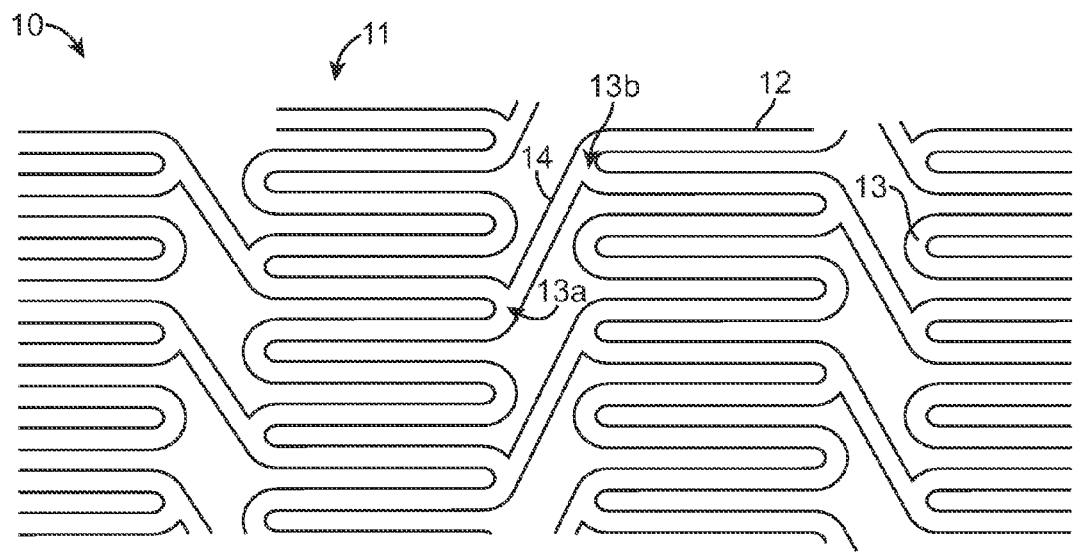
FIG. 1A is an unrolled view of an unexpanded stent.
Figure 1B:
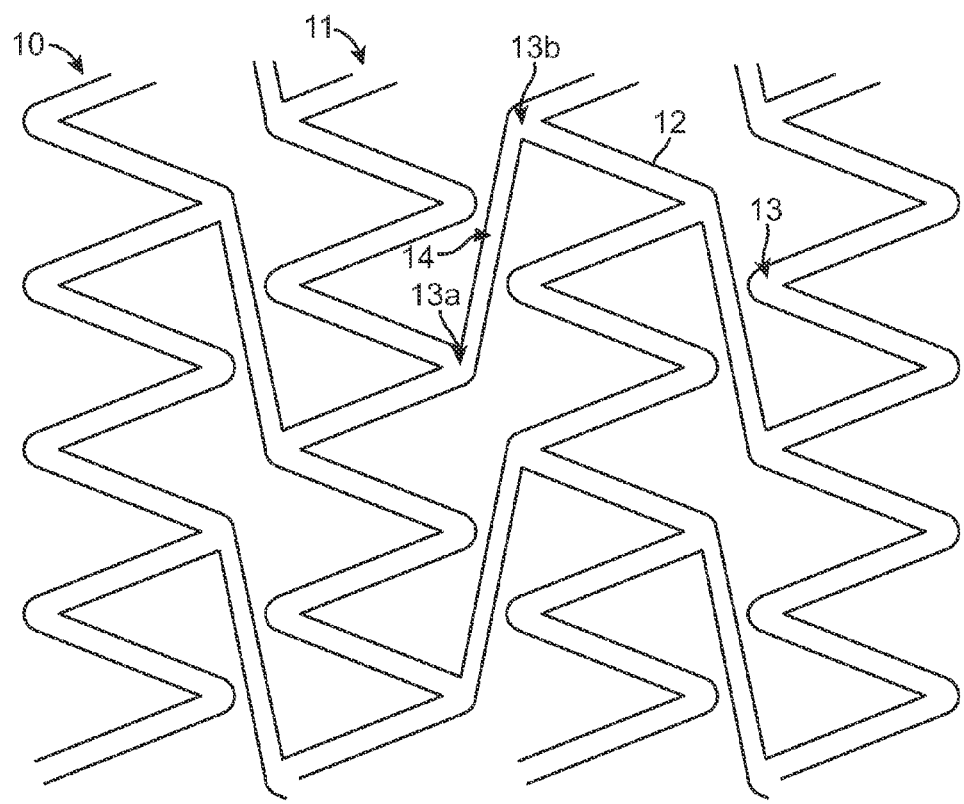
FIG. 1B is an unrolled view of the stent of FIG. 1A in its expanded configuration.

FIGS. 1A and 1B show a commercially available stent 10 in an unrolled view, for ease of description. FIGS. 1A and 1B show a portion of the stent 10 in its unexpanded and expanded configurations, respectively. Stent 10 may be balloon expandable or self-expanding and is usually between 2 mm and 200 mm in length, although other lengths are possible. Most stents according to embodiments of the present invention will be self-expanding. Stent 10 may also be coated with a therapeutic agent, for example, an anti-restenosis agent such as, Paclitaxel, Rapamycin or derivatives thereof such as Biolimus A9. Stent 10, like most stents, generally comprises a plurality of tubular rings 11 (shown in FIGS. 1A-1B in an unrolled view) arranged axially adjacent one another. Each of the tubular rings 11 can be radially contracted and expanded. Each tubular ring 11 comprises a plurality of axially oriented struts 12. In the contracted configuration, struts 12 are parallel to the longitudinal axis of the stent 10. Generally, struts 12, and therefore each of the tubular rings 11, all share the same shape (usually rectangular) and dimensions to allow for uniform compression and expansion of the stent 10 as a whole. Circumferentially adjacent struts 12 are connected at a common longitudinal end by a U-shaped connector 13. Connectors 13 are placed on alternating pairs of struts 12 thereby forming an undulating pattern of peaks having apices circumferentially aligned with one another. In the expanded configuration, the U-shaped connector 13 deflects outwardly so that the struts 12 form a undulating pattern of lower frequency when compared to the stent 10 in the collapsed configuration. FIG. 1B illustrates stent 10 in the expanded configuration. A bridge member 14 connects two axially adjacent tubular rings 11 together through adjacent connectors 13a, 13b. Bridge members 14 may be present for each connector 13, for every other connector 13, or in other alternating patterns. The bridge member 14 limits the axial flexibility of stent 10. For example, the greater the number of bridge members 14, the less the axial flexibility of stent 10. On the other hand, a longer or thinner bridge member 14 increases stent 10 flexibility. As shown in FIGS. 1A-B, bridge members 14 are generally straight and have alternating slopes between adjacent tubular rings 11 coupling staggered U-connectors 13 between adjacent tubular rings 11. Alternatively, bridge members 14 may all share the same slope or may all be parallel to the longitudinal axis of the stent. Besides being slanted as shown in FIGS. 1A-1B, bridge members 14 may also have different shapes. For example, bridge members 14 may be S-shaped, V-shaped, U-shaped, Z-shaped, etc. and these alternative geometries are well documented in medical and patent literature. Like most stents, its component parts including struts 12, connectors 13 and bridge members 14 are each integral parts of the stent and may be laser cut or EDM machined from tubing, or stent 10 may be photoetched from flat stock, with its ends rolled into a tube and welded together. While these commercially available designs are promising, stent flexibility still remains a challenge, especially when longer stents are required to treat long lesions or when stents are delivered in torturous vessels.

Figure 2A:
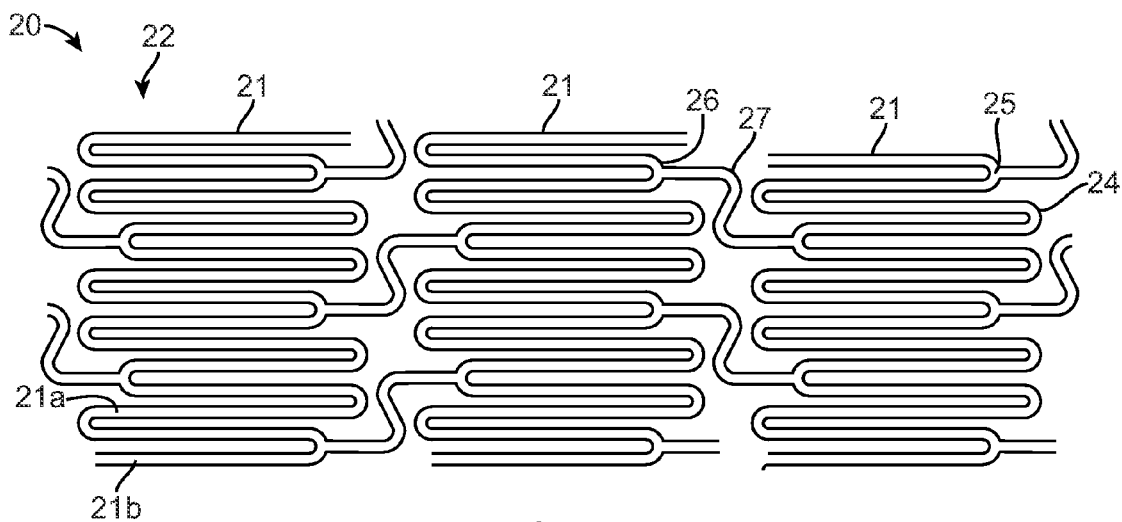
FIG. 2A is an unrolled view of an unexpanded stent having variable strut lengths and sigmoidal shaped bridge members.
Figure 2B:
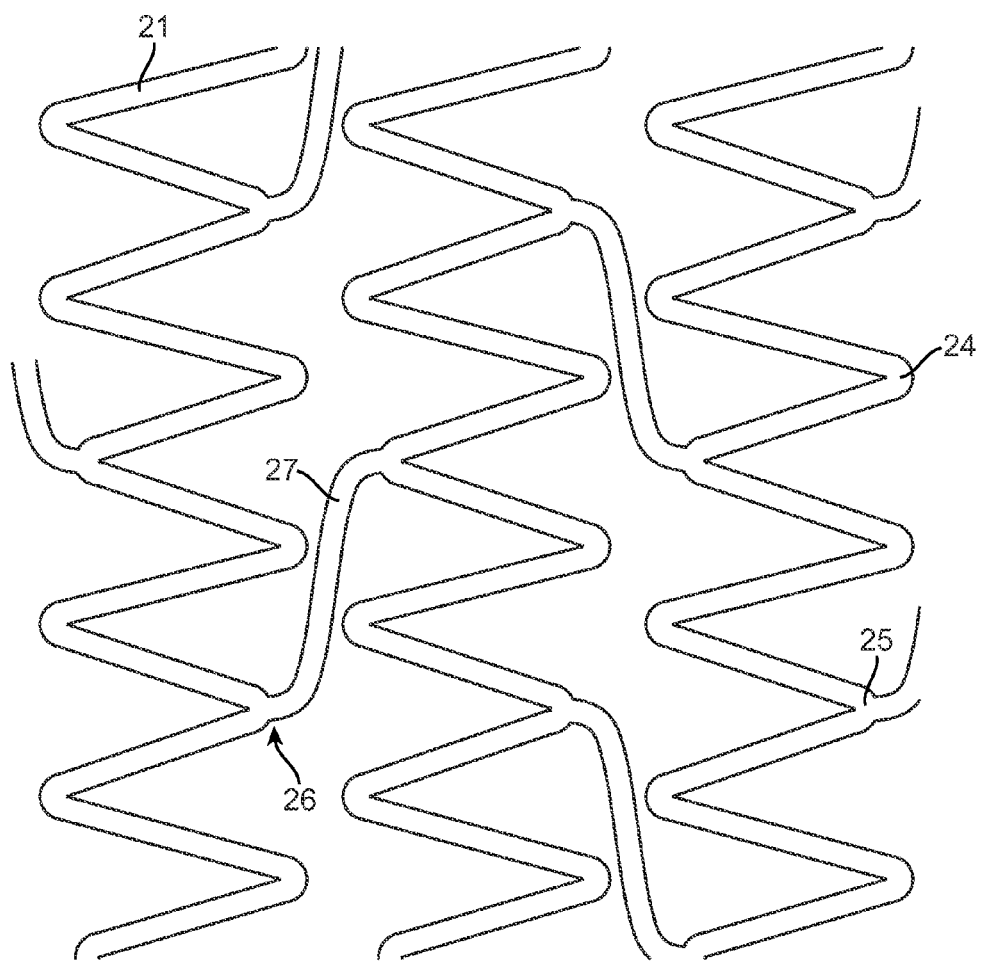
FIG. 2B is an unrolled view of the stent of FIG. 2A in its expanded configuration.

FIGS. 2A and 2B show a portion of a stent 20 according to an exemplary embodiment of the present invention. Stent 20 has improved flexibility and is shown in FIGS. 2A and 2B in its unexpanded state and its expanded state, respectively. Stent 20 is generally similar to the conventional stents described above with several exceptions noted below. Stent 20 is preferably a self-expanding stent fabricated from Nitinol although it may also be balloon expandable and fabricated from stainless steel, cobalt chromium alloy or other materials commonly used in balloon expandable stents. Stent 20 comprises tubular rings 22 which are connected together by bridge members 27. Each tubular ring 22 comprises several circumferentially adjacent struts 21. Although struts 21 are axially oriented and share the same rectangular shape, they are not of uniform length. Each of the tubular rings 22 comprises axially-oriented struts of alternating lengths. In the embodiments shown in FIGS. 2A-B, tubular rings 22 comprises long struts 21a and short struts 21b. Within each tubular ring 22, a long strut 21a is followed by a short strut 21b, which is then followed by another short strut 21b, which is then followed by a long strut 21a, and so forth. The ends of struts 21 are connected together with a U-shaped connectors 26 thereby forming a series of high peaks 24 and low peaks 25. The apices of the high peaks 24 are axially offset from the apices of the low peaks 25 but the apices of both peaks face in the same direction. In the exemplary embodiment of FIGS. 2A-2B, each low peak 25 is followed by two high peaks 24. Other strut arrangement patterns and strut lengths are also possible. Using struts of different, alternating lengths creates the high 24 and low peaks 25 which form a larger gap between adjacent rings 22 without significantly decreasing scaffolding ability of the stent 20. Scaffolding ability is maintained because the high peaks 24 still provide support in the gap region between adjacent tubular rings 22.

The larger gap created between low peaks 25 of stent 20 allow bridge members 27 to be axially longer than if all peaks were the same height as in a conventional stent, thereby creating a longer beam which can deflect more. This permits greater axial flexibility between adjacent tubular rings 22. As seen in FIGS. 2A-2B, sigmoidally shaped bridge member 27 spans between axially adjacent peaks 25 and is axially oriented ends couple to the apex of U-shaped connector 26. Bridge members 27 may also span between one low peak 25 and one high peak 24 to create a bridge member having intermediate length and therefore intermediate flexibility, as compared to a bridge member between two high peaks 24. A greater variety of strut lengths and therefore a greater variety of peak "heights" can also be used. One of ordinary skill in the art will recognize that the bridge member 27 may also couple with other portions of the tubular ring 22 including a region of peak 25 that is off-center from the apex 26 or laterally with strut 21. Additionally, any number of tubular rings 22 may be used in order to create a stent of varying length, although in this exemplary embodiment the overall stent length is preferably between about 2 mm and about 200 mm with individual tubular rings ranging from about 2 mm to about 5 mm long. Thus a stent may be composed of anywhere from 1 to 100 individual rings. FIG. 2B illustrates stent 20 in the expanded state.

Figure 3A:
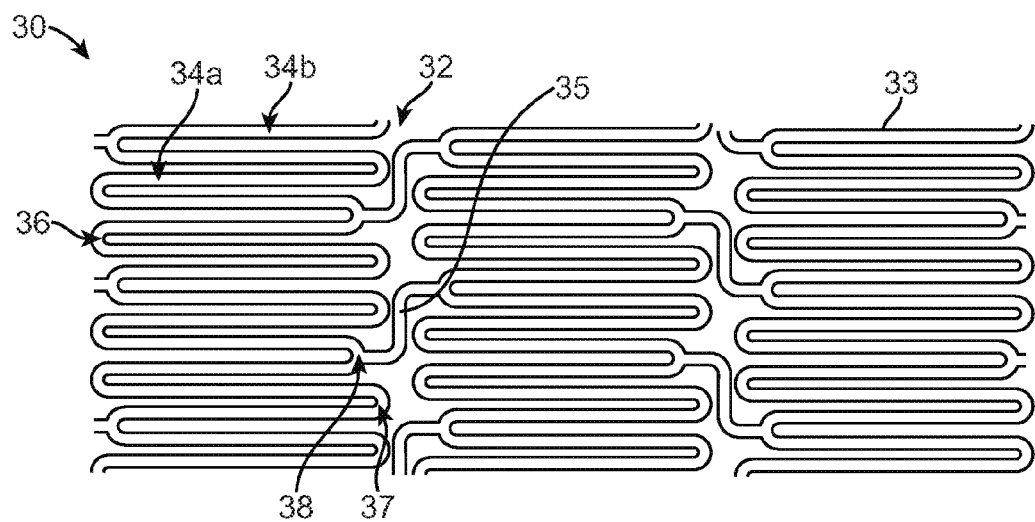
FIG. 3A is an unrolled view of an unexpanded stent having variable strut lengths and sigmoidal shaped bridge members with a transversely oriented portion.

FIG. 3A shows another exemplary embodiment of the present invention. Stent 30 is similar to the embodiment shown in FIGS. 2A-2B, with the major difference being the shape of its bridge member 32. In stent 30, each tubular ring 33 comprises long struts 34a and shorter struts 34b which are connected together with a U-shaped connector 36 thereby forming a plurality of high peaks 37 and low peaks 38. High peaks 37 are higher than the low peaks 38. Bridge member 32 is generally sigmoidally shaped and includes a transverse portion 35 generally perpendicular to the longitudinal axis of the stent 30. The bridge member 33 allows adjacent tubular rings 33 to flex relative to one another. The transverse portion 35 in bridge member 32 has a length greater than the circumferential distance between a peak on one tubular ring 33 and a peak on an adjacent tubular ring 33. Thus, the transverse portion 35 helps provide axial stability to the stent 30 during deployment. Often, stents are constrained by a protective outer sheath during delivery. As the outer sheath is retracted during stent delivery, friction between the sheath and the stent may cause adjacent ring sections of a stent to advance towards one another with ends potentially interleaving and overlapping, thereby causing binding between the stent and sheath during deployment. The transverse portion 35 extends circumferentially between adjacent tubular rings 33, therefore transverse portion 35 serves as a stop to prevent adjacent tubular rings 33 from overlapping with one another due to friction with a sheath during retraction and stent deployment. Therefore, using variable strut lengths allows a larger gap between adjacent tubular rings 33 to be created in order to accommodate the bridge member 32 having a transverse portion 35, resulting in a more axially stable stent 30.

Figure 3B:
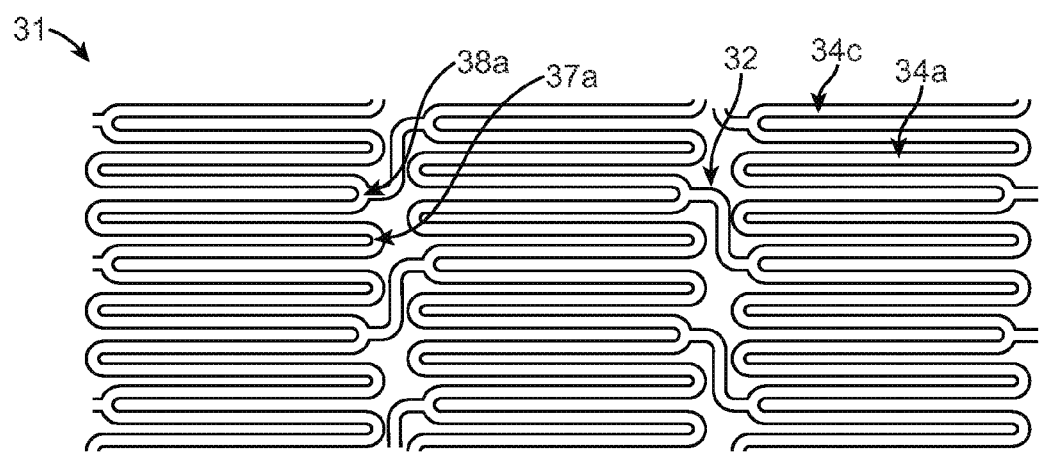
FIG. 3B is an unrolled view of a stent similar to that shown in FIG. 3A but with less variability in strut lengths.

FIG. 3B shows a stent similar to the embodiment of FIG. 3A with the major exception being that the height between high peaks 37a and low peaks 38a is less than the distance between high and low peaks 37, 38. Peak height is adjusted by varying the length of the axially oriented struts in stent 31. Stent 31 has long struts 34a and shorter struts 34c, yet in this embodiment strut 34c is longer than the short strut 34b in the previous embodiment. Reducing the height between high and low peaks 37a, 37b allows a bridge member 32 to be utilized having a shorter axial length than the embodiment of FIG. 3A, therefore axial rigidity of stent 31 may be adjusted as desired.

Figure 4A:
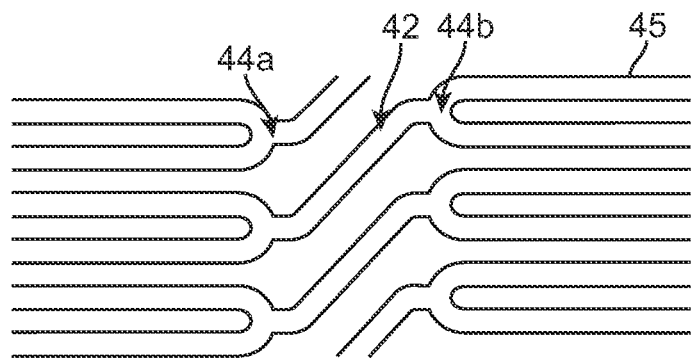
FIGS. 4A-4C show enlarged views of a stent having slanted bridge members under various operating conditions.
Figure 4B:
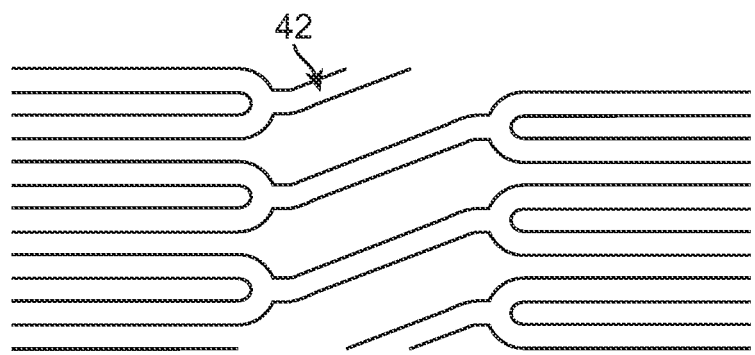
Figure 4C:
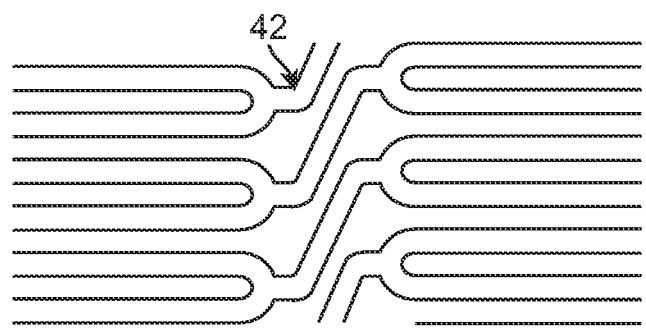
Figure 5A:
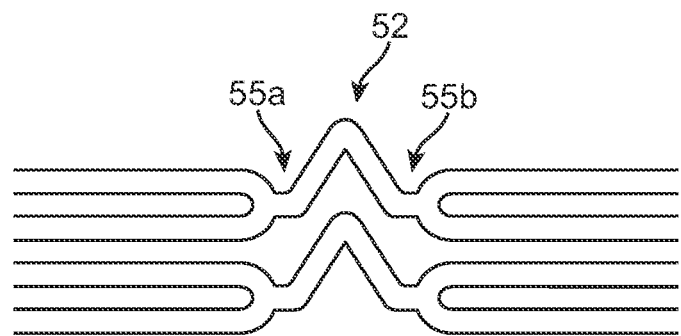
FIGS. 5A-5C show enlarged views of a stent having V-shaped bridge members under various operating conditions.
Figure 5B:
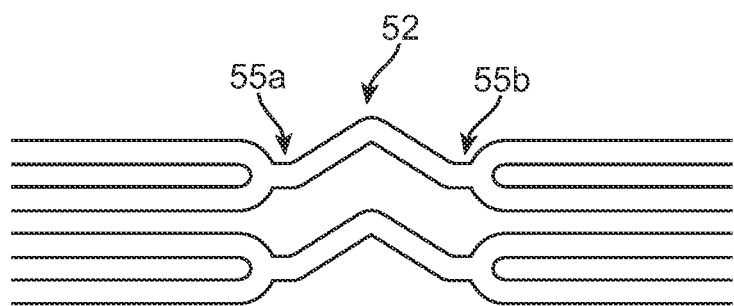
Figure 5C:
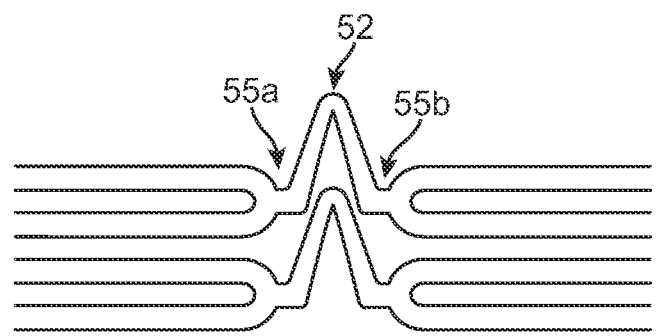

As previously described, conventional stents have bridge members which connect adjacent tubular rings. Several embodiments of bridge members that may be used in the stent embodiments previously disclosed are described herein below. FIGS. 4A-4C and FIGS. 5A-5C show the bridge members commonly used in existing stents and which may also be used in any of the embodiments described herein. FIGS. 4A, 4B and 4C show a sigmoidal bridge member 42 in a neutral, tensile and compressed configuration, respectively. Bridge member 42 spans between a connector 44a and a connector 44b. Connectors 44a, 44b link circumferentially adjacent struts 45 together. As shown in FIGS. 4A-4C, the peaks of connectors 44a and 44b may not share the same longitudinal axis and thus they are offset from one another. Therefore, any bridge member between the connectors is slanted relative to the longitudinal axis of the stent. FIGS. 5A-5C show bridge members 52 having a V-shape. FIGS. 5A, 5B and 5C show the bridge members 52 in a neutral, tensile and compressed configuration, respectively. Bridge member 52 spans between peaks of connectors 55a and 55b which share the same longitudinal axis. These and other bridge member shapes, such an "S", "U", "Z", etc., are used in conventional stents and can be used in embodiments of the present invention.

Figure 6:
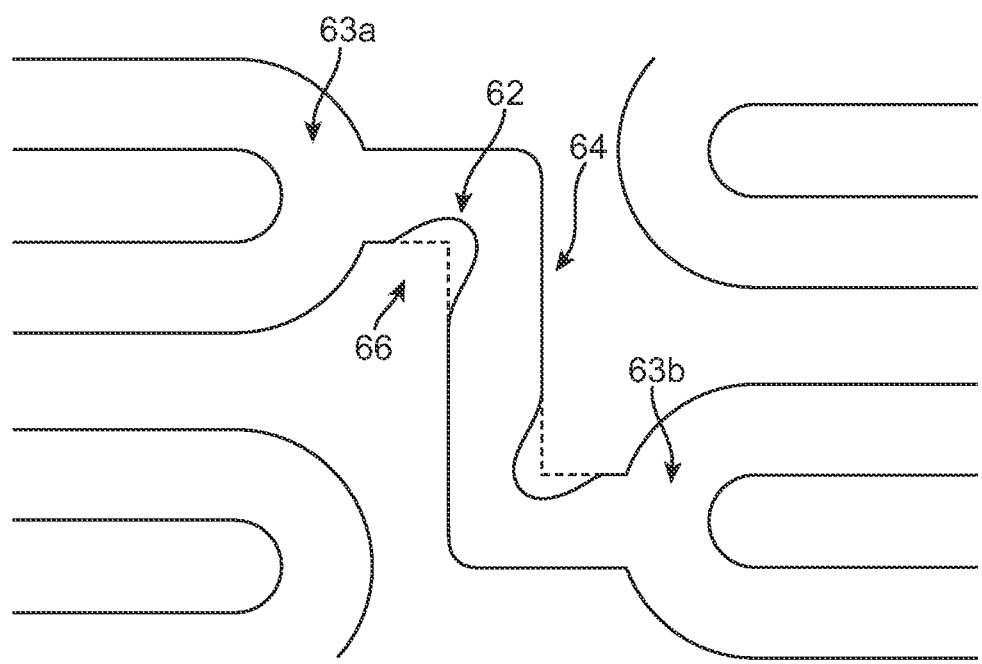
FIG. 6 shows a bridge member having strain relief regions.

An aspect of the present invention provides stent bridge members which increase the axial flexibility of the stent. FIG. 6 shows a bridge member 62 according to embodiments of the present invention. Bridge member 62 spans between axially adjacent peaks 63a and 63b and generally has two axially oriented sections coupled together with a transverse section 64 forming a stairway step shape. There are cut-away regions 66 (as marked by the dotted lines) located on the inside corners of the bridge member 62 as it transitions from being parallel to the longitudinal axis of the stent to being perpendicular. Cut-away regions 66 are strain relief regions which increase the flexibility of bridge member 62. Cut-away regions may alternatively be located on other regions of the bridge member 62.

FIGS. 7A and 7B-1 and 7B-2 show another bridge member 72, and associated cross-sectional views respectively, according to embodiments of the present invention. Conventional stents have a uniform thickness throughout. Bridge member 72 has an arcuate surface thinner than the thickness of struts 74 and connectors 77. This is best seen in FIG. 7B-1 which shows a cross section of bridge member 72 taken along line 7B-7B between adjacent connectors 77a and 77b. The arcuate surface may be created by grinding material away from the original surface 72a of bridge member 72 using techniques such as laser ablation, sanding, water blasting, or the like. The bridge member 72 is thus thinner and has greater flexibility. As shown in FIG. 7B, the cross-section of bridge member 72 is concave on one side and convex on the opposite side. Alternatively, bridge member 72 may be curved on only one side as shown in alternate cross section in FIG. 7B-2. Other bridge member geometries may also be used. For example bridge member 72 may have a thicknesses less than that of the struts and connectors, or the overall width of the bridge member 72 can also be reduced as seen in FIG. 7C. In both cases, increased flexibility of the stent results from a thinner bridge member.

Figure 8:
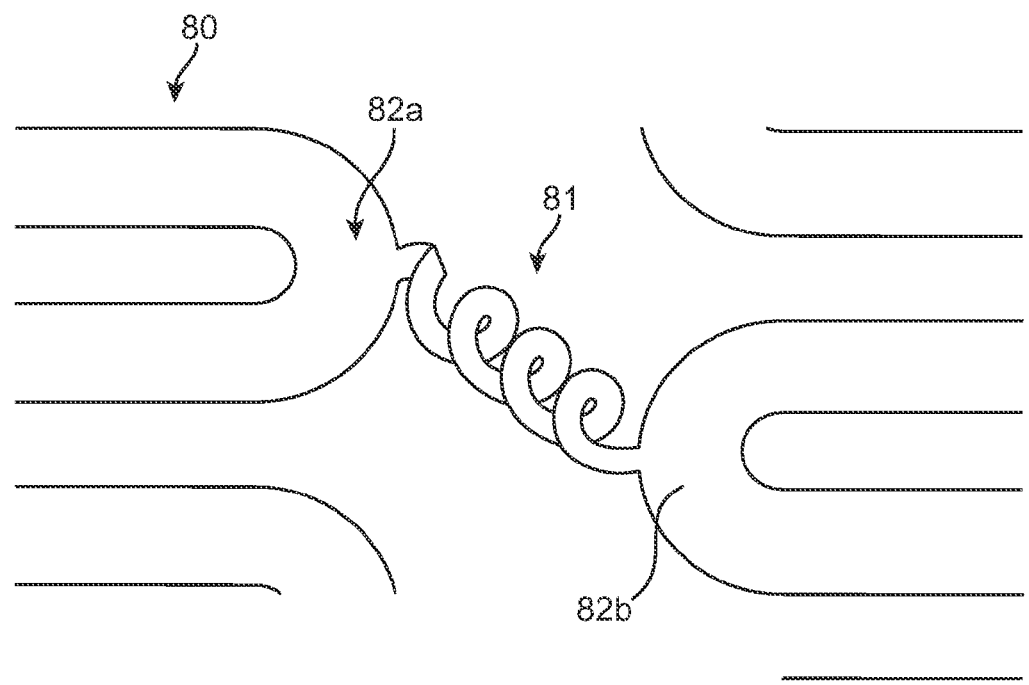
FIG. 8 shows a spring-like bridge member.

FIG. 8 shows another bridge member according to embodiments of the present invention. Bridge member 81 is spring-like and thus provides a high degree of flexibility in all directions. Unlike the bridge members previously described which are cut from the same material as the remainder of the stent, bridge member 81 may be laser cut and then formed separately over adjacent strut connectors 82a and 82b. Bridge member 81 may then be welded, bonded or otherwise attached to adjacent tubular stent rings thereby coupling them together.

Figure 9:
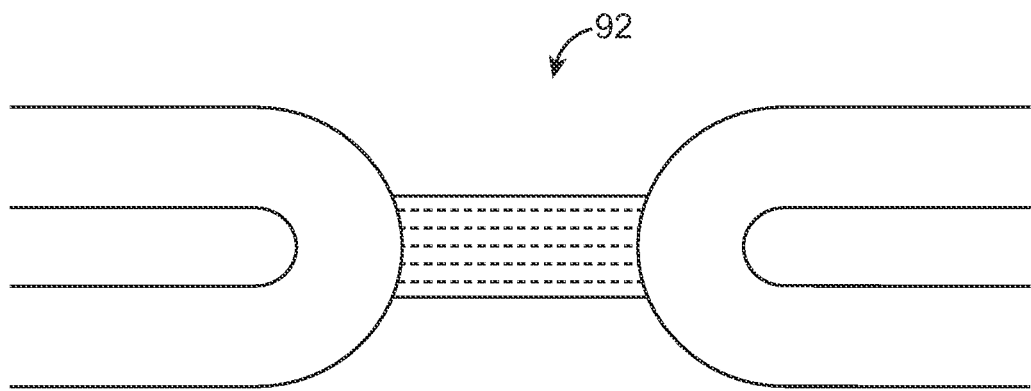
FIG. 9 shows an elastomeric bridge member.

FIG. 9 shows another bridge member according to embodiments of the present invention. In this embodiment, bridge member 92 comprises an elastomer which can be resiliently stretched in any direction, thus increasing the axial flexibility of the stent. For example, the elastomer may be rubber or a rubber-like material such as synthetic rubber and latex.

Figure 10A:
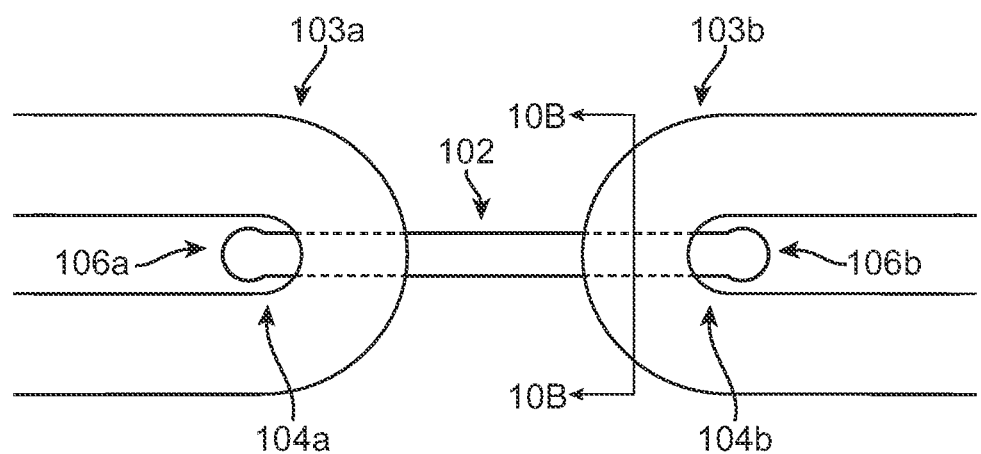
FIG. 10A shows a bridge member slidably engaged with struts of adjacent tubular rings.
Figure 10B:
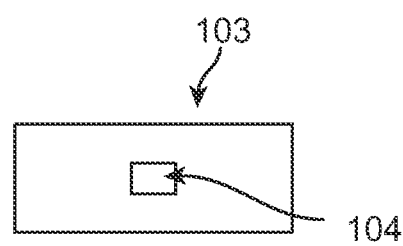
FIG. 10B is a side-view of the strut in FIG. 10A.

FIGS. 10A-10B show another bridge member according to embodiments of the present invention. Bridge member 102 traverses between strut connectors 103a and 103b. FIG. 10B shows a cross section of a strut connector 103 taken along line 10B-10B. Strut connector 103 has a longitudinal aperture 104 in a plane generally parallel to the outer surface of the stent. Bridge member 102 traverses between strut connectors 103a and 103b and is received in apertures 104a and 104b, thus slidably coupling the two. Bridge member 102 also includes end portion 106a, 106b on each of its two longitudinal ends. Enlarged head regions 106a, 106b have a greater cross-sectional area than aperture 104a, 104b, restricting the axial movement of the connectors 103a and 103b relative to one another. Head regions 106a, 106b may be formed for example by folding the ends of the bridge member over itself or welding the enlarged region to the axial portion of bridge member 102.

Figure 11A:
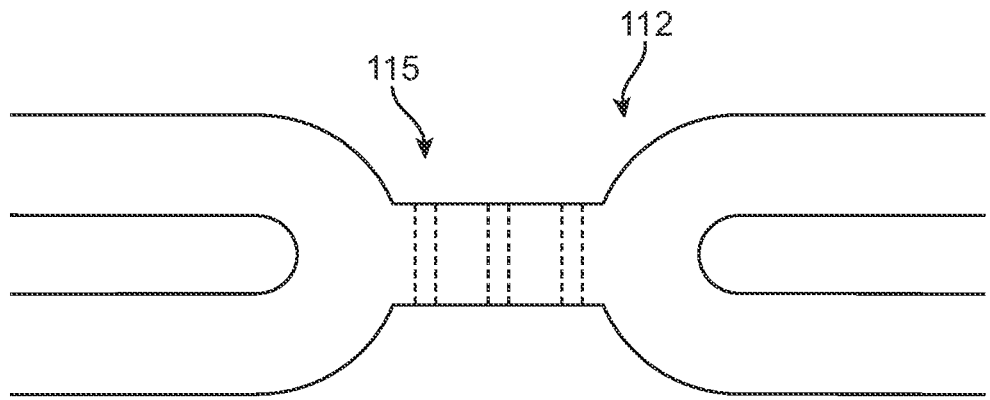
FIGS. 11A-11C show top and side views of a bridge member having an aperture.
Figure 11B:
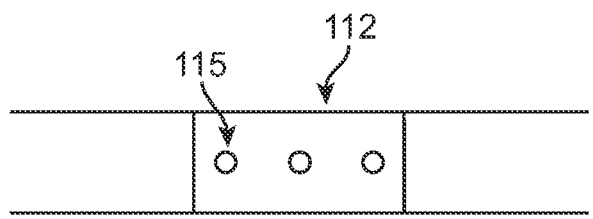
Figure 11C:
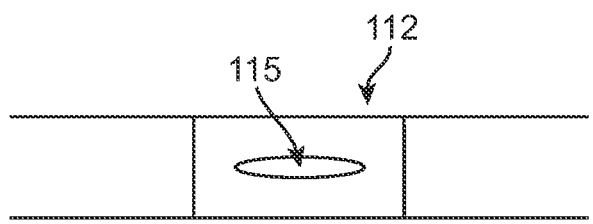

FIGS. 11A-11C show another bridge member according to embodiments of the present invention. Bridge member 112 has at least one aperture 115 through its width. The apertures 115 have an axis that is generally parallel to the outer surface of the stent. FIG. 11B is a side-view of FIG. 11A and shows three apertures while FIG. 11C is also a side-view of FIG. 11A and shows an alternative embodiment having an oval-shaped aperture. Other shapes and numbers of apertures may be used as well. Having at least one aperture through the width of the bridge member 112 increases the overall flexibility of the stent.

Figure 12:
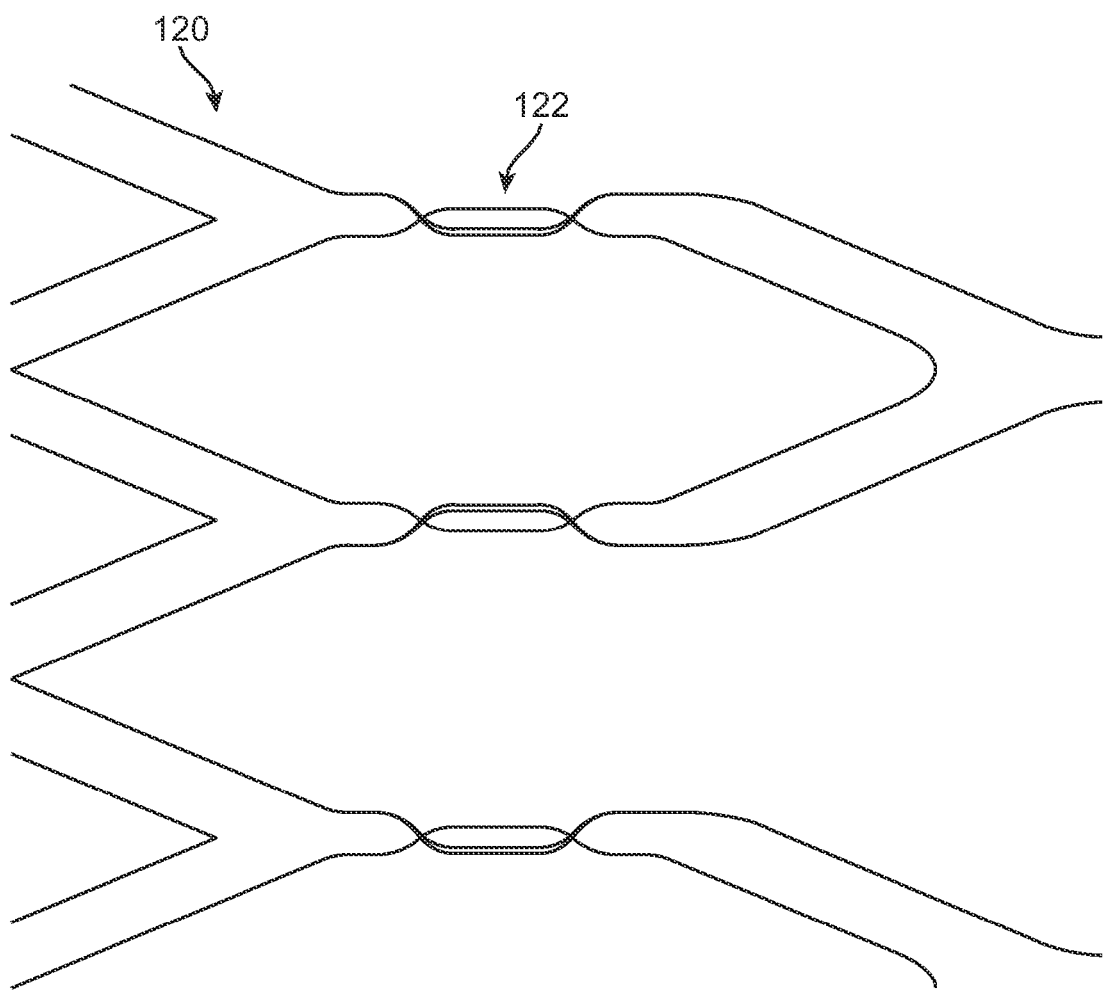
FIG. 12 is a magnified view of a stent having helical bridge members.

FIG. 12 shows a portion of a stent 120 having bridge members according to another embodiment of the present invention. Helical bridge member 122 comprises a bar having a section rotated approximately 90 degrees and a second section rotated another 90 degrees to form a helix with portions of the bar generally in two planes that are orthogonal to one another. Helical bridge member 122 may also be formed by a bar rotated multiple times. By rotating the bridge in such a manner, helical bridge member 122 has a greater degree of axial flexibility than a simple single plane bridge member without sacrificing the radial strength of the stent. The bridge member 122 may be formed separately from the remainder of the stent 120 and then welded or otherwise attached thereto in a secondary process, or individual bridge members 122 may be helically rotated in an integrally formed stent.

Figure 13:
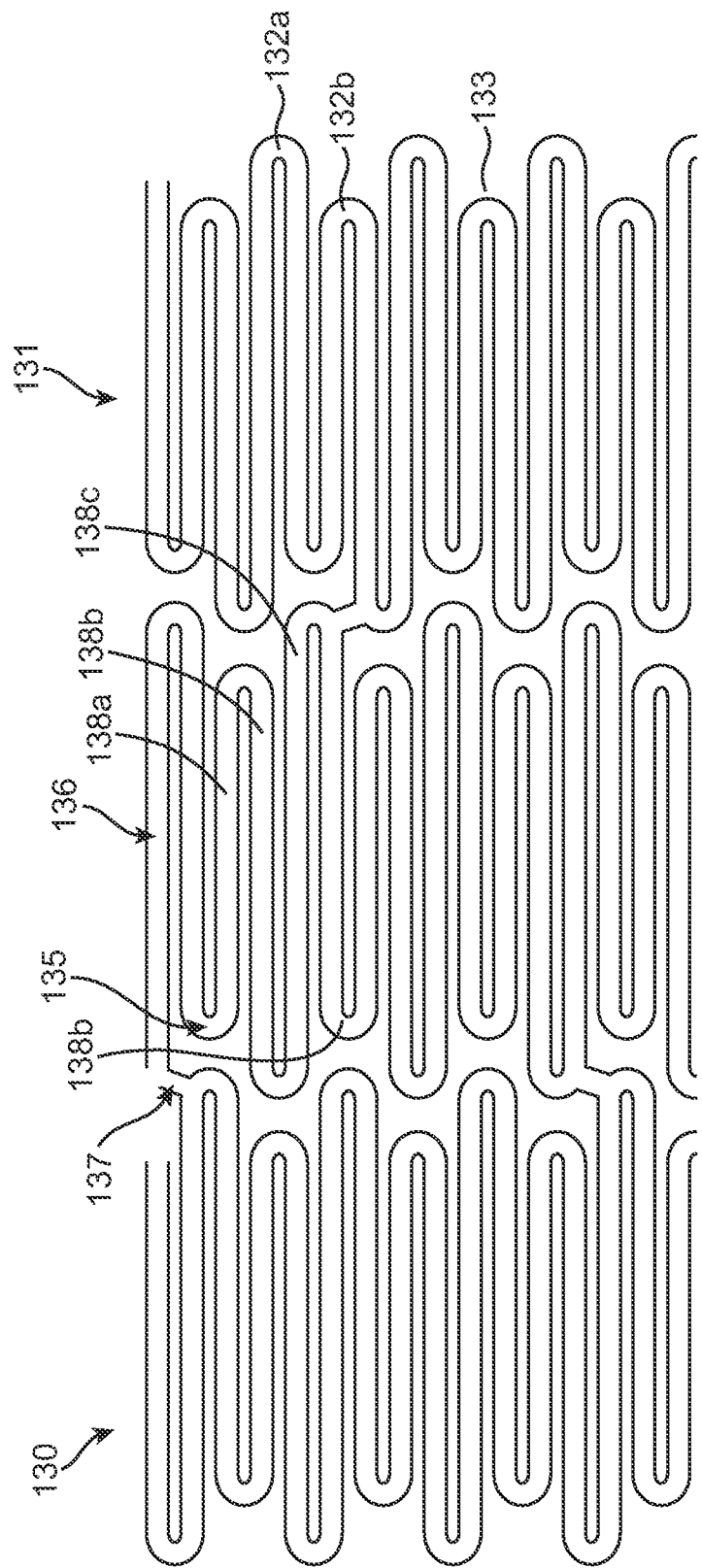
FIG. 13 is an unrolled view of a stent having interleaving adjacent tubular rings.

FIG. 13 shows yet another embodiment a stent having variable strut lengths in order to produce a more flexible stent. This embodiment is similar to previous embodiments with the major difference being that the gap created by high and low peaks is used to allow adjacent tubular rings to overlap or interleave with one another. Adjacent tubular rings are coupled together with a shorter bridge connector. FIG. 13 is a rolled out view of a stent 130 having interleaving peaks. Stent 130 comprises a plurality of tubular rings 131 each having low 132b and high peaks 132a. The tubular rings are in close, axial proximity with one another such that the peak of one of the tubular rings is nested between the recess 133 formed by two peaks of an adjacent tubular ring. In other words, the peaks interleave, providing better stability for the stent 130 in its compressed or crimped state. Because of the enhanced stability of the stent 130, fewer bridge members are required to couple adjacent tubular rings 131 together, thus the overall stent is more flexible even though shorter bridge members are used. As with the embodiments previously described, the peaks 132a, 132b are formed by U-shaped connectors 135 which connect circumferentially adjacent struts 136. A short, bridge member 137 is occasionally formed laterally between adjacent peaks. In other words, the bridge members 137 are attached to connectors on areas of the connector offset from the apex of its peak. Overall length of stent 130 is similar to that disclosed for previous embodiments and thus stent 130 ranges in length from about 2 mm to about 200 mm.

The circumferentially adjacent struts 136 of stent 130 form a repeating sequence of four struts having three different lengths. The sequence comprises a short length strut 138a followed by a medium length strut 138b which is then followed by a long length strut 138c which is followed by another medium length strut 138b.

In preferred embodiments of FIG. 13, strut thickness is constant throughout each tubular ring and strut width is varied. The longest strut 138c has the largest strut width, the shortest strut 138a has the smallest strut width, and the intermediate length struts 138b have a width in between the width of the longest and shortest struts 138c and 138a. This configuration helps to ensure uniform strut expansion and thus uniform vessel scaffolding. In still other embodiments, variable strut thickness may be employed exclusively or in combination with variable strut width and variable strut length.

FIGS. 14A-14C illustrate an exemplary method of deploying the stents disclosed herein. In FIG. 14A, a single stent 1506 is disposed over a catheter shaft 1504 in delivery system 1500. In other embodiments, multiple stents may be carried by the catheter shaft 1504. Delivery system 1500 is introduced and advanced in an artery V over a guidewire GW to lesion L using standard catheterization techniques well known in the art. Stent 1506 is a self-expanding prosthesis having multiple tubular rings coupled together and interleaving with one another as illustrated in FIG. 13. Outer sheath 1502 constrains stent 1506 and prevents it from expanding until it is properly positioned adjacent lesion L in vessel V. Once the physician has properly positioned stent 1506, outer sheath 1502 is retracted relative to pusher tube 1512 allowing stent 1506 to self-expand into its expanded configuration 1508 into lesion L. FIG. 14B shows expanded stent 1508 after the sheath 1502 has been retracted. In some embodiments, stent 1506 may also be coated, impregnated, infused or otherwise coupled with one or more drugs that inhibit restenosis, such as Rapamycin, Everolimus, Biolimus A9, Paclitaxel, derivates, prodrugs, or derivatives of the aforementioned, or other suitable agents, preferably carried in a durable or bioerodable carrier of polymeric or other suitable material. Alternatively, the stent 1506 may be coated with other types of drugs or therapeutic materials such as antibiotics, thrombolytics, anti-thrombotics, anti-inflammatories, cytotoxic agents, anti-proliferative agents, vasodilators, gene therapy agents, radioactive agents, immunosuppressants, chemotherapeutics, endothelial cell attractors or promoters and/or stem cells. Such materials may be coated over all or a portion of the surface of the stent or the stent may have a porous structure or include apertures, holes, channels, or other features in which such materials may be deposited.

Additionally, as previously mentioned, delivery catheter 1500 in this exemplary embodiment only carries a single stent 1506. However, in other embodiments, delivery catheter 1500 may carried multiple stents. For example, a delivery catheter 1500 may carry two stents 1506, 1510. After the first stent is deployed at a first lesion as seen in FIG. 14B, the delivery catheter 1500 may be repositioned to another lesion L as seen in FIG. 14C. Outer sheath 1502 may then be retracted again, allowing the second stent 1510 to self-expand into the second lesion, L. In addition to deploying multiple stents at multiple sites, multiple stents may also be deployed at a single treatment site, thereby customizing stent length. Additional disclosure relating to systems which may be for deployment of customized stent lengths, including any of the stents disclosed herein is disclosed in U.S. Patent Publication Nos. 2007/0027521 and 2006/0282150, the entire contents of which are incorporated herein by reference. Additionally, delivery systems which may be used with any of the stents disclosed herein and which may help to control stent delivery due to the tendency of the stent to jump away from the delivery catheter are disclosed in U.S. patent application Ser. No. 11/752,448, the entire contents of which are also incorporated herein by reference.

While the exemplary embodiments have been described in some details for clarity of understanding and by way of example, a variety of additional modifications, adaptations and changes may be clear to those of skill in the art. Hence, the scope of the present invention is limited solely by the appended claims.

What is claimed is:

1. A tubular prosthesis comprising:
a plurality of tubular rings radially expandable from a contracted configuration to an expanded configuration, each ring comprising a plurality of axially oriented struts interconnected so as to form a plurality of high peaks and a plurality of low peaks, the plurality of high peaks and the plurality of low peaks being circumferentially arranged to form an alternating series of at least one high peak and at least one low peak, the high and low peaks having apices oriented in the same axial direction, the apices of the high peaks being axially offset from the apices of the low peaks, the apices of the high peaks being axially aligned with one another, the apices of low peaks being axially aligned with one another; and
at least one non-linear bridge member coupling each pair of adjacent tubular rings together, the at least one non-linear bridge member having a first end connected to a first low peak in a first tubular ring of a respective pair of adjacent tubular rings and a second end connected to a second low peak in a second tubular ring of the respective pair of adjacent tubular rings, and a non-linear intermediate portion extending between the first and second ends, wherein the non-linear intermediate portion includes a transverse portion extending in a direction perpendicular to a longitudinal axis of the tubular prosthesis when the prosthesis is in the contracted configuration,
wherein the apices of the high and low peaks in the first tubular ring are circumferentially offset from the apices of the high and low peaks in the second tubular ring such that the first low peak in the first tubular ring is circumferentially offset from the second low peak in the second tubular ring, and
wherein each and every bridge member of the prosthesis extends circumferentially between adjacent unconnected high peaks of the first and second adjacent tubular rings of the respective pair of adjacent tubular rings connected by the respective bridge member and extends a length greater than a circumferential distance between the respective adjacent unconnected high peaks of the respective pair of adjacent tubular rings such that the respective bridge member inhibits contact between and overlapping of the adjacent unconnected high peaks of the respective adjacent tubular rings during flexure of the tubular prosthesis in the contracted configuration,
wherein the non-linear bridge member includes a portion, between the first end and the second end, having a reduced thickness by curving inward on only one side to facilitate flexibility between the first and second tubular rings coupled with the non-linear bridge member.

2. The tubular prosthesis of claim 1, wherein each high peak comprises a long strut having a first length and each low peak comprises a short strut having a second length shorter than the first length.

3. The tubular prosthesis of claim 1, wherein the plurality of axially oriented struts comprise long struts and short struts, the short struts shorter than the long struts and wherein the plurality of axially oriented struts are arranged circumferentially such that each short strut is disposed between one long strut and one short strut.

4. The tubular prosthesis of claim 1, wherein the low and the high peaks are arranged circumferentially such that each high peak is disposed between one low peak and one high peak.

5. The tubular prosthesis of claim 1, wherein the apices of the high and low peaks of the first tubular ring point toward the apices of the high and low peaks of the second tubular ring.

6. The tubular prosthesis of claim 1, wherein the first low peak is circumferentially offset from the high peak in the second tubular ring.

7. The tubular prosthesis of claim 1, wherein each low peak comprises two short struts.

8. The tubular prosthesis of claim 1, wherein each high peak comprises one long strut and one short strut, the short strut shorter than the long strut.

9. The tubular prosthesis of claim 1, wherein each high peak comprises one long strut and one short strut, the long strut having a first width and the short strut having a second width less than the first.

10. The tubular prosthesis of claim 1, wherein the bridge member is sigmoidal shaped.

11. The tubular prosthesis of claim 1, wherein the bridge member has a z-shape.

12. The tubular prosthesis of claim 1, wherein the bridge member comprises a surface defining one or more apertures therein.

13. The tubular prosthesis of claim 12, wherein the apertures extend entirely through the bridge member.

14. The tubular prosthesis of claim 12, wherein the apertures have an axis parallel to an outer surface of the prosthesis.

15. The tubular prosthesis of claim 12, wherein at least one of the apertures form an elongate slot.

16. The tubular prosthesis of claim 1, wherein the bridge member has a thickness in a radial direction, the thickness varying across the bridge member.

17. The tubular prosthesis of claim 1, wherein the bridge member, from the first end to the second end, defines a step shape and further includes a strain relief region, the strain relief region comprising an area with a reduced width where the bridge member transitions from being parallel to the longitudinal axis to being perpendicular to the longitudinal axis.

18. The tubular prosthesis of claim 1, wherein the bridge member has a first radial thickness and the plurality of axially oriented struts have a second radial thickness different than the first thickness.

19. The tubular prosthesis of claim 18, wherein the first radial thickness is less than the second radial thickness.

20. The tubular prosthesis of claim 1, wherein the bridge member comprises a resilient elastomer.

21. The tubular prosthesis of claim 1, wherein adjacent struts of each of the tubular rings of the plurality are connected by a connector, and the bridge member is slidably engaged with the connector.

22. The tubular prosthesis of claim 1, wherein the bridge member comprises a first axially oriented portion such that the transverse portion extends transverse to the first axially oriented portion and is coupled thereto.

23. The tubular prosthesis of claim 22, wherein the bridge member further comprises a second axially oriented portion, the transverse portion disposed between the first and second axially oriented portions.

24. The tubular prosthesis of claim 1, wherein the bridge member has an axial length between the first and second ends longer than the axial distance between high peaks on adjacent tubular rings.

25. The tubular prosthesis of claim 1, wherein the bridge member has an axial length between the first and second ends longer than the axial distance between a high peak and a low peak on adjacent tubular rings.

26. The tubular prosthesis of claim 1, wherein the first tubular ring is disposed between the second tubular ring and a third tubular ring, the first tubular ring being connected to the third tubular ring by a second bridge member.

27. The tubular prosthesis of claim 26, wherein the bridge member has a first orientation and the second bridge member has a second orientation, wherein the second orientation is a mirror image of the first orientation.

28. The tubular prosthesis of claim 26, wherein the bridge member has a first slope and the second bridge member has a second slope, the second slope being opposite the first slope.

29. The tubular prosthesis of claim 1, wherein the first end of the bridge member connects to the first low peak at the apex thereof.

30. The tubular prosthesis of claim 1, wherein the second end of the bridge member connects to the apex of the low peak in the adjacent tubular ring.

31. The tubular prosthesis of claim 1, further comprising a therapeutic agent carried by the prosthesis and adapted to being released therefrom at a controlled rate.

32. The tubular prosthesis of claim 1, wherein the plurality of tubular rings are self-expanding.

33. The tubular prosthesis of claim 1, wherein the tubular prosthesis has a length in the range from about 2 mm to about 200 mm.

34. The tubular prosthesis of claim 1, wherein each of the plurality of tubular rings has the same axial length.

35. The tubular prosthesis of claim 1, further comprising a third tubular ring adjacent the first tubular ring and unconnected thereto.

36. The tubular prosthesis of claim 35, further comprising a fourth tubular ring unconnected to but deployable with the first or third tubular ring.

37. The tubular prosthesis of claim 1, wherein the entire transverse portion is oriented perpendicular to the longitudinal axis of the tubular prosthesis, the transverse portion being disposed between a first peak on the first tubular ring and a second peak on the second tubular ring thereby preventing the first peak from overlapping with the second peak when the tubular prosthesis is in compression.

38. The tubular prosthesis of claim 1, wherein the bridge member comprises an axial portion and a circumferential portion transverse thereto.

39. The tubular prosthesis of claim 1, wherein the bridge member has a width equivalent to a width of the axial struts.

40. The tubular prosthesis of claim 1, wherein the bridge member comprises a first axially oriented region which includes the first end, and a second axially oriented region which includes the second end.

41. The tubular prosthesis of claim 1, wherein the plurality of struts are parallel when in the contracted configuration.

42. The tubular prosthesis of claim 1, wherein the bridge member comprises two axially oriented sections coupled together with a transverse section forming a step shape.

43. A tubular prosthesis comprising:
a plurality of tubular rings radially expandable from a contracted configuration to an expanded configuration, each ring comprising a plurality of axially oriented struts interconnected so as to form a plurality of high peaks and a plurality of low peaks, the plurality of high peaks and the plurality of low peaks being circumferentially arranged to form an alternating series of high peaks and low peaks, the high and low peaks having apices oriented in the same axial direction, the apices of the high peaks being axially offset from the apices of the low peaks, the apices of the high peaks being substantially axially aligned with one another, the apices of the low peaks being substantially axially aligned with one another,
wherein each strut of the plurality has a width and is connected to a circumferentially adjacent strut of the plurality of struts at a common longitudinal end by a U-shaped connector,
wherein each pair of adjacent tubular rings of the plurality of tubular rings are circumferentially offset from one another such that a high peak on a first tubular ring of a respective pair of adjacent tubular rings is disposed circumferentially between two high peaks on a second tubular ring of the respective pair of adjacent tubular rings along a longitudinal axis of the prosthesis; and
a plurality of bridge members coupling each pair of adjacent tubular rings together, each and every bridge member having a first end connected to a low peak of the first tubular ring and a second end connected to a low peak of the adjacent tubular ring,
wherein the first end of the bridge member is circumferentially offset from the second end of the bridge member,
wherein each bridge member has a non-linear intermediate portion extending between the first and second ends,
wherein the non-linear intermediate portion includes a transverse portion extending in a direction perpendicular to the longitudinal axis of the tubular prosthesis when the prosthesis is in the contracted configuration,
wherein each and every bridge member of the prosthesis extends circumferentially between adjacent unconnected high peaks of first and second adjacent tubular rings of the respective adjacent pair of tubular rings connected by the respective bridge member and extends a length greater than a circumferential distance between the respective adjacent unconnected high peaks of the respective pair of adjacent tubular rings such that the respective bridge member inhibits contact between and overlapping of the unconnected adjacent high peaks of the respective adjacent tubular rings during flexure of the tubular prosthesis in the contracted configuration, wherein the non-linear bridge member includes a portion, between the first end and the second end, having a reduced thickness by curving inward on only one side to facilitate flexibility between the first and second tubular rings coupled with the non-linear bridge member.

44. The tubular prosthesis of claim 43, wherein each high and low peak is separated from an adjacent high or low peak by a valley, and wherein the circumferential width of each valley in the contracted configuration is less than the circumferential width of each peak in the contracted configuration.

45. The tubular prosthesis of claim 43, wherein the high and low peaks circumferentially alternate with one another in the first tubular ring.

46. The tubular prosthesis of claim 43, wherein the apices of the high and low peaks in the first tubular ring are circumferentially offset from the apices of the high and low peaks in the adjacent tubular ring.

47. The tubular prosthesis of claim 43, wherein each high peak comprises a long strut having a first length and each low peak comprises a short strut having a second length shorter than the first length.

48. The tubular prosthesis of claim 43, wherein the plurality of axially oriented struts comprise long struts and short struts, the short struts shorter than the long struts and wherein the plurality of axially oriented struts are arranged circumferentially such that each short strut is disposed between one long strut and one short strut.

49. The tubular prosthesis of claim 48, wherein the long struts have a first width and the short struts have a second width less than the first width.

50. The tubular prosthesis of claim 43, wherein the low and the high peaks are arranged circumferentially such that each high peak is disposed between two low peaks.

51. The tubular prosthesis of claim 43, wherein the apices of the high and low peaks of the first tubular ring point toward the apices of the high and low peaks of the adjacent tubular ring.

52. The tubular prosthesis of claim 43, wherein each high and low peak is separated from an adjacent high or low peak by a valley, and wherein the high peaks on the first tubular ring are nested between valleys on the adjacent tubular ring.

53. The tubular prosthesis of claim 43, wherein the apices of the low peaks in the first tubular ring are circumferentially aligned with the apices of the high peaks in the adjacent tubular ring.

54. The tubular prosthesis of claim 43, wherein the first tubular ring is disposed between the adjacent tubular ring and a third tubular ring, the first tubular ring being connected to the third tubular ring with a second bridge member.

55. The tubular prosthesis of claim 54, wherein the bridge member has a first orientation and the second bridge member has a second orientation, wherein the second orientation is a mirror image of the first orientation.

56. The tubular prosthesis of claim 43, wherein the first end of the bridge member connects to a portion of a first peak offset from the apex thereof in the first tubular ring.

57. The tubular prosthesis of claim 43, wherein the second end of the bridge member connects to a portion of a peak offset from the apex thereof in the adjacent tubular ring.

58. The tubular prosthesis of claim 43, further comprising a therapeutic agent carried by the prosthesis and adapted to being released therefrom at a controlled rate.

59. The tubular prosthesis of claim 43, wherein the plurality of tubular rings are self-expanding.

60. The tubular prosthesis of claim 43, wherein the tubular prosthesis has a length in the range from about 2 mm to about 200 mm.

61. The tubular prosthesis of claim 43, wherein each of the plurality of tubular rings has the same axial length.

62. The tubular prosthesis of claim 43, further comprising a third tubular ring adjacent the first tubular ring and unconnected thereto.

63. The tubular prosthesis of claim 62, further comprising a fourth tubular ring unconnected to but deployable with the first or third tubular ring.

64. The tubular prosthesis of claim 43, wherein each of the high peaks has the same shape and dimension as an adjacent high peak on each ring.

* * * * *